US010899827B2

(12) United States Patent
Rabbani et al.

(10) Patent No.: US 10,899,827 B2
(45) Date of Patent: *Jan. 26, 2021

(54) ANTIBODIES SPECIFIC FOR SULFATION SITES OF SCLEROSTIN

(71) Applicant: Enzo Biochem, Inc., New York, NY (US)

(72) Inventors: Joshua Rabbani, New York, NY (US); James J. Donegan, Long Beach, NY (US)

(73) Assignee: Enzo Biochem, Inc., New York, NY (US)

(*) Notice: Subject to any disclaimer, the term of this patent is extended or adjusted under 35 U.S.C. 154(b) by 349 days.

This patent is subject to a terminal disclaimer.

(21) Appl. No.: 15/273,000

(22) Filed: Sep. 22, 2016

(65) Prior Publication Data
US 2017/0066820 A1 Mar. 9, 2017

Related U.S. Application Data

(63) Continuation of application No. 13/088,059, filed on Apr. 15, 2011, now Pat. No. 9,493,541, which is a continuation-in-part of application No. 12/802,447, filed on Jun. 7, 2010, now Pat. No. 9,617,323.

(51) Int. Cl.
C07K 16/22 (2006.01)
C07K 14/47 (2006.01)
C07K 14/51 (2006.01)
C07K 14/705 (2006.01)
C07K 14/71 (2006.01)

(52) U.S. Cl.
CPC .............. C07K 16/22 (2013.01); C07K 14/47 (2013.01); C07K 14/51 (2013.01); C07K 14/705 (2013.01); C07K 14/71 (2013.01); C07K 2317/54 (2013.01); C07K 2317/55 (2013.01); C07K 2317/76 (2013.01)

(58) Field of Classification Search
None
See application file for complete search history.

(56) References Cited

U.S. PATENT DOCUMENTS

| | | | |
|---|---|---|---|
| 4,895,452 A | 1/1990 | Yiournas | |
| 4,921,706 A | 5/1990 | Roberts | |
| 7,585,501 B2 | 9/2009 | Krumlauf et al. | |
| 9,403,882 B2* | 8/2016 | Rabbani | C07K 14/47 |
| 9,493,541 B2* | 11/2016 | Rabbani | C07K 14/47 |
| 9,617,323 B2* | 4/2017 | Rabbani | C07K 14/47 |
| 2004/0009535 A1 | 1/2004 | Brunkow | |
| 2004/0038860 A1 | 2/2004 | Allen et al. | |
| 2005/0163776 A1 | 7/2005 | Raven et al. | |
| 2005/0196349 A1 | 9/2005 | Wu et al. | |
| 2006/0030523 A1 | 2/2006 | Wu et al. | |
| 2006/0127393 A1 | 6/2006 | Li et al. | |
| 2006/0198791 A2 | 9/2006 | Wu | |
| 2006/0233801 A1* | 10/2006 | Brunkow | C07K 14/51 424/145.1 |
| 2007/0110747 A1 | 5/2007 | Paszty et al. | |
| 2007/0154472 A1 | 7/2007 | Widom et al. | |
| 2007/0299009 A1 | 12/2007 | Dong et al. | |
| 2008/0119402 A1 | 5/2008 | Zheng et al. | |
| 2009/0130113 A1 | 5/2009 | Kneissel et al. | |
| 2010/0298200 A1 | 11/2010 | Liu et al. | |
| 2011/0300159 A1 | 12/2011 | Rabbani et al. | |
| 2012/0071399 A1 | 3/2012 | Rabbani et al. | |

FOREIGN PATENT DOCUMENTS

| | | |
|---|---|---|
| WO | WO2005/003158 | 1/2005 |
| WO | WO2005003158 | 1/2005 |
| WO | WO2005/095448 | 10/2005 |

(Continued)

OTHER PUBLICATIONS

Lloyd et al. (Protein Engineering, Design & Selection 2009, 22:159-168).*
Campbell (Monoclonal Antibody Technology, 1984, Chapter 1, pp. 1-32).*
Baum et al. Clinic Rev Allerg Immunolo 2016, 51:1-15.*
Cha et al., "Wnt11/5a Complex Formation Caused by Tyrosine Sulfation Increases Canonical Signaling Activity," Current Biology, vol. 19, pp. 1573-1580 (2009).
Craig, "Production and Characterization of Monoclonal Antibodies to Human Sclerostin," Hybridoma, vol. 28, No. 5, pp. 377-381 (2009).
European Patent Application No. 18173173, European search Report and Information on Search Strateay (2018).
Moester et al., "Sclerostin: Current Knowledge and Future Perspectives" Calcif Tissue Int, vol. 87, pp. 99-107 (2010).

(Continued)

Primary Examiner — Sharon X Wen
(74) Attorney, Agent, or Firm — Paul Diamond, Esq.

(57) ABSTRACT

Provided is a protein comprising an antibody binding site that binds to a sulfated epitope of a Wnt pathway protein that is not Wnt5A, Wnt11, or Wnt3a. Also provided is a composition comprising an isolated and purified Wnt pathway protein, where the protein is sulfated but not glycosylated. Additionally provided is a preparation of a Wnt pathway protein comprising at least one sulfation site and at least one glycosylation site, where all of the Wnt pathway protein in the preparation is glycosylated but not sulfated. Further provided is a composition comprising a peptide less than 75 amino acids or amino acid analogs, the peptide consisting of a fragment of a Wnt pathway protein, wherein the fragment is sulfated. A modified Wnt pathway protein comprising a sulfation site that is not present in the native Wnt pathway protein is also provided. Also provided is a method of detecting or quantifying a sulfated Wnt pathway protein in a preparation. Additionally, a modified Wnt pathway protein lacking a sulfation site that is present in the native Wnt pathway protein is provided. Also provided is methods of treating a subject having a disease exacerbated by Wnt activation. Additionally, a method of treating a subject having a disease exacerbated by Wnt inhibition is provided.

4 Claims, 8 Drawing Sheets

Specification includes a Sequence Listing.

(56) References Cited

FOREIGN PATENT DOCUMENTS

| | | |
|---|---|---|
| WO | WO2006/119107 | 11/2006 |
| WO | WO2011/156252 | 12/2011 |
| WO | WO2012/058393 | 5/2012 |

OTHER PUBLICATIONS

Monigatti et al., "The Sulfinator: predicting tyrosine sulfation sites in protein sequences," *Applications Note*, vol. 18, No. 5, pp. 769-770 (2002).

Rider et al., "Bone Morphogenetic protein and growth differentiation factor cytokine families and their protein antagonists," *Biochem J.*, vol. 429, pp. 1-12 (2010).

Seibert et al., "Toward a Framework for Sulfoproteomics: Synthesis and Characterization of Sulfotyrosine-Containing Peptides," *Peptide Science*, vol. 90, No. 3, pp. 459-477 (2007).

Veverka et al., "Characterization of the Structural Features and Interactions of Sclerostin," *Journal of Biological Chemistry*, vol. 284, No. 16, pp. 10890-10900 (2009).

Chen et al., Activation of the Wnt Pathway Plays a Pathogenic Role in Diabetic Retinopathy in Humans and Animal Models, Am. J. Pathol. 2009, 2676-2685, 175.

Kasinathan et al., Inhibition of Tyrosylprotein Sulfotransferase by Sphingosine and Its Reversal by Acidic Phospholipids, Biochemistry 1993, 1194-1198, 32.

Kasinathan et al., Effect of Sofalcone on Tyrosylprotein Sulfotransferase, Gen. Pharmacol, 1994, 1017-1020, 25.

Polakis, Paul, Wnt signaling and cancer, Genes Dev. 2000, 1837-1851, 14.

Woods et al., Sulfation, the Up-and-Coming Post-Translational Modification: Its Role and Mechanism in Protein-Protein Interaction, J. Proteome Res. 2007, 1176-1182, 6.

Baeuerle and Huttner, Cholorate—A potent inhibitor of protein sulfation in intact cells, BBRC 1986, 870-877, 141.

Baeuerle and Huttner, Tyrosine Sulfation of Yolk Proteins 1, 2, and 3 in *Drosophila melanogaster*, J. Biol. Chem. 1985, 6434-6439, 260.

Banner et al., Crystal Structure of the Soluble Human 55 kd TNF Receptor-Human TNF Beta Complex: Implications for TNF Receptor Activation, Cell, 1993, 431-445, 73.

Borghei et al., Targeted Disruption of Tyrosylprotein Sulfotransferase-2, an Enzyme That Catalyzes Post-translational Protein Tyrosine O-Sulfation, Causes Male Infertility, J. Biol. Chem. 2006, 9423-9431, 281.

Bundgaard et al., New Consensus Features for Tyrosine O-Sulfation Determined by Mutational Analysis, J. Biol. Chem. 1997, 21700-21705, 272.

Bundgaard et al., Analysis of Tyrosine-O-Sulfation, Methods Mol Bio 2008, 47-66, 446.

Cha et al., Wnt11/5a Complex Formation Caused by Tyrosine Sulfation Increases Canonical Signaling Activity, Current Biol 2009, 1573-1580, 19.

Colvin et al., CXCR3 Requires Tyrosine Sulfation for Ligand Binding and a Second Extracellular Loop Arginine Residue for Ligand-Induced Chemotaxis, Molec Cell Biol 2006, 5838-5849, 26.

Cormier et al., Specific interaction of CCR5 amino-terminal domain peptides containing sulfotyrosines with HIV-1 envelope glycoprotein gp120, Proc. Nat. Acad. Sci USA 2000, 5762-5767, 97.

Costagliola et al. Tyrosine sulfation is required for agonist recognition by glycoprotein hormone receptors, EMBO J 2002, 504-513, 21.

Craig et al., Sclerostin binds and regulates the activity of cysteine-rich protein 61, BBRC 2010, 36-40, 392.

Craig et al., Production and Characterization of Monoclonal Antibodies to Human Sclerostin, Hybridoma 2009, 377-381, 28.

Digiovanna et al., Production of Antibodies That Recognize Specific Tyrosine-Phosphorylated Peptides, Current Protocols in Cell Biology 2002, 16.6.1-16.6.18.

Drake and Hortin, Improved detection of intact tyrosine sulfate-containing peptides by matrix-assisted laser desorption/ionization time-of-flight mass spectrometry in linear negative ion mode, Int J Biochem Cell Biol 2010, 174-179, 42.

Farzan et al., Tyrosine Sulfation of the Amino Terminus of CCR5 Facilitates HIV-1 Entry, Cell 1999, 667-676, 96.

Farzan et al., Sulfated Tyrosines Contribute to the Formation of the C5a Docking Site of the Human C5a Anaphylatoxin Receptor, J Exp Med 2001, 1059-1065, 193.

Feng et al., Sulfotyrosines of the Kaposi's Sarcoma-Associated Herpesvirus G Protein-Coupled Receptor Promote Tumorigenesis through Autocrine Activation, J Vir 2010, 3351-3361, 84.

Fieger et al., Type 1 sphingosine 1-phosphate G protein-coupled receptor signaling of lymphocyte functions requires sulfation of its extracellular amino-terminal tyrosines, FASEB J 2005, 1926-1928, 19.

Gao et al., Sulfation of Tyrosine 174 in the Human C3a Receptor Is Essential for Binding of C3a Anaphylatoxin, J. Biol. Chem. 2003, 37902-37908, 278.

Gorr and Cohn, Secretion of Sulfated and Nonsulfated Forms of Parathyroid Chromogranin A (Secretory Protein-I), J. Biol. Chem. 1990, 3012-3016, 265.

Gutierrez et al., Analysis of Post-translational CCR8 Modifications and Their Influence on Receptor Activity, J. Biol. Chem. 2004, 14726-14733, 279.

Hammond et al., Beta Strand Peptidomimetics as Potent PDZ Domain Ligands, Chem & Biol 2006, 1247-1251, 13.

Hemmerich et al., Strategies for drug discovery by targeting sulfation pathways, Drug Discovery Today 2004, 967-975, 9.

Hilsted and Rehfeld, alpha-Carboxyamidation of Antral Progastrin , J. Biol. Chem. 1987, 16953-16957, 262.

Hirata et al., Human P-selectin Glycoprotein Ligand-1 (PSGL-1) Interacts with the Skin-associated Chemokine CCL27 via Sulfated Tyrosines at the PSGL-1 Amino Terminus, J. Biol. Chem. 2004, 51775-51782, 279.

Hoffhines et al., Detection and Purification of Tyrosine-sulfated Proteins Using a Novel Anti-sulfotyrosine Monoclonal Antibody, J. Biol. Chem. 2006, 37877-37887, 281.

Hortin et al., Inhibitors of the sulfation of proteins, glycoproteins and proteoglycans, BBRC 1988, 342-348, 150.

Huang and Honda, CED: a conformational epitope database, BMC Immunology, 2006, 7:7.

Huttner et al., Determination and Occurrence of Tyrosine O-Sulfate in Proteins, Meth Enzymol 1984, 200-223, 107.

Itkonen et al., Mass spectrometric detection of tyrosine sulfation in human pancreatic trypsinogens, but not in tumor-associated trypsinogen, FEBS Journal 2008, 289-301, 275.

Jekel et al., Dimerization of an antigenic peptide leads to strong interaction with its antibody, Biochimica Biophysica Acta 1996, 195-198, 1291.

Kehoe and Bertozzi, Tyrosine sulfation: a modulator of extracellular protein-protein interactions, Chemistry & Biology 2000, R57-R61, 7.

Kehoe et al., Using Phage Display to Select Antibodies Recognizing Post-translational Modifications Independently of Sequence Context, Molec Cell Proteomics 2006, 2350-2363, 5.

Kehoe et al., Tyrosylprotein sulfotransferase inhibitors generated by combinatorial target-guided ligand assembly, Bioorg Med Chem Letters 2002, 329-332, 12.

Liu et al. Tyrosine Sulfation Is Prevalent in Human Chemokine Receptors Important in Lung Disease, Am J Resp Cell Molec Biol 2008, 738-743, 38.

Ma and Geng, Obligatory Requirement of Sulfation for P-Selectin Binding to Human Salivary Gland Carcinoma Acc-M Cells and Breast Carcinoma ZR-75-30 Cells, J Immunol 2002, 1690-1696, 168.

Medzihradszky et al., O-Sulfonation of Serine and Threonine, Molec Cell Proteomics 2004, 429-443, 3.

Mintz et al., Chlorate-induced Inhibition of Tyrosine Sulfation on Bone Sialoprotein Synthesized by a Rat Osteoblast-like Cell Line (UMR 106-01 BSP), J. Biol. Chem. 1994, 4845-4852, 269.

Monigatti et al., Protein sulfation analysis—A primer, Biochim Biophys Acta 2006, 1904-1913, 1764.

(56) References Cited

OTHER PUBLICATIONS

Monigatti et al. The sulfinator: predicting tyrosine sulfation sites in protein sequences, Bioinformatics 2002, 769-770, 18.

Moreau et al., Discontinuous epitope prediction based on mimotope analysis, Bioinformatics 2006, 1088-1095, 22.

Niehrs et al., Analysis of the Substrate Specificity of Tyrosylprotein Sulfotransferase Using Synthetic Peptides, J. Biol. Chem. 1990, 8525-8532, 265.

Onnerfjord et al., Identification of Tyrosine Sulfation in Extracellular Leucine-rich Repeat Proteins Using Mass Spectrometry, J. Biol. Chem. 2004, 26-33, 279.

Ouyang et al., Reduced Body Weight and Increased Postimplantation Fetal Death in Tyrosylprotein Sulfotransferase-1-deficient Mice, J. Biol. Chem. 2002, 23781-23787, 277.

Rehfeld et al., Cell-specific processing of pro-cholecystokinin and pro-gastrin, Biochimie 1988, 25-31, 70.

Seibert and Sakmar, Toward a Framework for Sulfoproteomics: Synthesis and Characterization of Sulfotyrosine-Containing Peptides, Biopolymers, 2008, 459-477, 90.

Stone et al., Tyrosine sulfation: an increasingly recognised post-translational modification of secreted proteins, New Biotechnology 2009, 299-317, 25.

Van Regenmortel, From absolute to exquisite specificity. Reflections on the fuzzy nature of species, specificity and antigenic sites, J Immunol Methods 1998, 37-48, 216.

Veverka et al., Characterization of the Structural Features and Interactions of Sclerostin, J. Biol. Chem. 2009, 10890-10900, 284.

Villen et al., Synthetic Peptides as Functional Mimics of a Viral Discontinuous Antigenic Site, Biologicals 2001, 265-269, 29.

Weidauer et al. NMR structure of the Wnt modulator protein Sclerostin, BBRC 2009, 160-165, 380.

Westmuckett et al., Early postnatal pulmonary failure and primary hypothyroidism in mice with combined TPST-1 and TPST-2 deficiency, Gen. Compar. Endocrine 2008, 145-153, 156.

Winkler et al., Osteocyte control of bone formation via sclerostin, a novel BMP antagonist, EMBO J 2003, 6267-6276, 22.

Winkler et al., Noggin and Sclerostin Bone Morphogenetic Protein Antagonists Form a Mutually Inhibitory Complex, J. Biol. Chem. 2004, 36293-36298, 279.

Chan, Sze Lai Celine, Sclerostin: a negative regulator of bone formation and a target for osteoporosis therapy, Sclerostin : a negative regulator of bone formation and a target for osteoporosis therapy, 2009, 83-84, Ph.D. Thesis, University of Hong Kong.

MacDonald et al., Wnt/beta-catenin signaling: components, mechanisms, and diseases, Developmental Cell, 2009, 9-26, 17.

Zhong et al., Regulation of secreted frizzled-related protein-1 by heparin, JBC 2007, 20523-20533, 282.

Moester et al., Sclerostin: Current Knowledge and Future Perspectives, Calcif. Tissue Int., 2010, 99-107, 87.

Skolnick et al., "From genes to protein structure and function: novel applications of computational approaches in the genomic era," TIBTECH, vol. 18, pp. 34-29 (2000).

Attwood, Teresa K., "The Babel of Bioinformatics," *Science*, vol. 290, pp. 471-473 (2000).

Gregory et al., "Dkk-1-derived Synthetic Peptides and Lithium Chloride for the Control and Recovery of Adult Stem Cells from Bone Marrow," *J. Biol. Chem.*, vol. 280, pp. 2309-2323.

Lee et al., "Intranasal delivery of proteins and peptides," *Bioharm.*, pp. 30-37 (1988).

Murrills et al., A Cell-Based Dkk1 Binding Assay Reveals Roles for Extracellular Domains of LRP5 in Dkk1 Interaction and Highlights Differences Between Wild-Type and the High Bone Mass Mutant LRP5(G171V), *J. Cellular Biochem.*, vol. 108, pp. 1066-1075 (2009).

Stevenson, Advances in Peptide Pharmaceuticals, *Curr. Phar. Biotechnol.*, vol. 10, pp. 122-137 (2009).

Ruben et al., AB023445 Standard: Peptide: 15 AA, XP-002758468, Amino acid sequence #85 associated with human secreted proteins (Sep. 4, 2003).

Chan, Sze Lai Celine, "Scierostin—A Negative Regulator of Bone Formation and a Target for Osteoporosis Therapy," Thesis for Doctor of Philosophy Degree at the University of Hong Kong (2009).

\* cited by examiner

FIG. 4

SEQUENCE LISTING

```
<160> NUMBER OF SEQ ID NOS: 27

<210> SEQ ID NO 1
<211> LENGTH: 12
<212> TYPE: PRT
<213> ORGANISM: Homo sapiens

<400> SEQUENCE: 1

Leu Gly Glu Tyr Pro Glu Pro Pro Glu Leu Glu
1               5                   10

<210> SEQ ID NO 2
<211> LENGTH: 8
<212> TYPE: PRT
<213> ORGANISM: Homo sapiens

<400> SEQUENCE: 2

Tyr Val Thr Asp Gly Pro Cys Arg
1               5

<210> SEQ ID NO 3
<211> LENGTH: 10
<212> TYPE: PRT
<213> ORGANISM: Homo sapiens
```

-continued

<400> SEQUENCE: 3

Ala Asn Gln Ala Glu Leu Glu Asn Ala Tyr
1               5                   10

<210> SEQ ID NO 4
<211> LENGTH: 16
<212> TYPE: PRT
<213> ORGANISM: Homo sapiens

<400> SEQUENCE: 4

Glu Leu Gly Glu Tyr Pro Glu Pro Pro Glu Leu Glu Asn Asn Lys
1               5                   10                  15

<210> SEQ ID NO 5
<211> LENGTH: 16
<212> TYPE: PRT
<213> ORGANISM: Mus sp.

<400> SEQUENCE: 5

Gly Leu Gly Glu Tyr Pro Glu Pro Pro Glu Asn Asn Gln Thr Met
1               5                   10                  15

<210> SEQ ID NO 6
<211> LENGTH: 16
<212> TYPE: PRT
<213> ORGANISM: Rattus sp.

<400> SEQUENCE: 6

Gly Leu Arg Glu Tyr Pro Glu Pro Pro Gln Glu Leu Glu Asn Asn Gln
1               5                   10                  15

<210> SEQ ID NO 7
<211> LENGTH: 14
<212> TYPE: PRT
<213> ORGANISM: Homo sapiens

<400> SEQUENCE: 7

Glu Leu Gly Glu Tyr Pro Glu Pro Pro Glu Leu Glu Asn
1               5                   10

<210> SEQ ID NO 8
<211> LENGTH: 11
<212> TYPE: PRT
<213> ORGANISM: Homo sapiens

<400> SEQUENCE: 8

Lys Ala Asn Gln Ala Glu Leu Glu Asn Ala Tyr
1               5                   10

<210> SEQ ID NO 9
<211> LENGTH: 13
<212> TYPE: PRT
<213> ORGANISM: Homo sapiens

<400> SEQUENCE: 9

Glu Leu Gly Glu Tyr Pro Glu Pro Pro Glu Leu Glu
1               5                   10

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10 cagggggtggc aggcgttcaa        20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtaggcgttc tccagctcgg        20

<210> SEQ ID NO 12
<211> LENGTH: 9
<212> TYPE: PRT
<213> ORGANISM: Homo sapiens

<400> SEQUENCE: 12

Ile Ile Tyr His Met Asp Glu Glu Glu
1               5

<210> SEQ ID NO 13
<211> LENGTH: 12
<212> TYPE: PRT
<213> ORGANISM: Homo sapiens

<400> SEQUENCE: 13

Asp Asn Tyr Gln Pro Tyr Pro Cys Ala Glu Asp Glu
1               5                   10

<210> SEQ ID NO 14
<211> LENGTH: 9
<212> TYPE: PRT
<213> ORGANISM: Mus sp.

<400> SEQUENCE: 14

Asp Leu Asp Asn Tyr Gln Pro Tyr Pro
1               5

<210> SEQ ID NO 15
<211> LENGTH: 12
<212> TYPE: PRT
<213> ORGANISM: Homo sapiens

<400> SEQUENCE: 15

Gly Asn Asn Phe Asp Tyr Trp Lys Tyr Gly Glu Ala
1               5                   10

<210> SEQ ID NO 16
<211> LENGTH: 11
<212> TYPE: PRT
<213> ORGANISM: Homo sapiens

<400> SEQUENCE: 16

Pro Asp Tyr Trp Lys Tyr Gly Glu Ala Ser Ser
1               5                   10

<210> SEQ ID NO 17
<211> LENGTH: 16
<212> TYPE: PRT
<213> ORGANISM: Homo sapiens

<400> SEQUENCE: 17

Ile Thr Ser His Asp Tyr Leu Gly Gln Glu Thr Leu Thr Glu Ile Gln
1               5                   10                  15

<210> SEQ ID NO 18
<211> LENGTH: 15
<212> TYPE: PRT
<213> ORGANISM: Mus sp.

<400> SEQUENCE: 18

Ile Ala Asp His Asp Tyr Leu Gly Gln Glu Thr Ser Thr Glu Val
1               5                   10                  15

<210> SEQ ID NO 19
<211> LENGTH: 11
<212> TYPE: PRT
<213> ORGANISM: Homo sapiens

<400> SEQUENCE: 19

Ala Ile Ala Ile Asp Tyr Asp Pro Leu Glu Gly
1               5                   10

<210> SEQ ID NO 20
<211> LENGTH: 16
<212> TYPE: PRT
<213> ORGANISM: Homo sapiens

<400> SEQUENCE: 20

Pro His Ser Gln Tyr Leu Ser Ala Glu Asp Ser Cys Pro Pro Ser Pro
1               5                   10                  15

<210> SEQ ID NO 21
<211> LENGTH: 16
<212> TYPE: PRT
<213> ORGANISM: Mus sp.

<400> SEQUENCE: 21

Thr Ser Asp Val Asn Tyr Asp Ser Glu Pro Val Pro Pro Thr Pro
1               5                   10                  15

<210> SEQ ID NO 22
<211> LENGTH: 188
<212> TYPE: PRT
<213> ORGANISM: Homo sapiens

<400> SEQUENCE: 22

Trp Gln Ala Phe Lys Asn Asp Ala Thr Glu Ile Ile Pro Glu Leu Gly
1               5                   10                  15

Glu Tyr Pro Glu Pro Pro Pro Glu Leu Glu Asn Asn Lys Thr Met Asn
                20                  25                  30

Arg Ala Glu Asn Gly Gly Arg Pro Pro His His Pro Phe Glu Thr Lys
            35                  40                  45

Asp Val Ser Glu Tyr Ser Cys Arg Glu Leu His Phe Thr Arg Tyr Val
        50                  55                  60

Thr Asp Gly Pro Cys Arg Ser Ala Lys Pro Val Thr Glu Leu Val Cys
65                  70                  75                  80

Ser Gly Gln Cys Gly Pro Ala Arg Leu Leu Pro Asn Ala Ile Gly Arg
                85                  90                  95

Gly Lys Trp Trp Arg Pro Ser Gly Pro Asp Phe Arg Cys Ile Pro Asp
            100                 105                 110

```
Arg Tyr Arg Ala Gln Arg Val Gln Leu Leu Cys Pro Gly Gly Glu Ala
            115                 120                 125

Pro Arg Ala Arg Lys Val Arg Leu Val Ala Ser Cys Lys Cys Lys Arg
        130                 135                 140

Leu Thr Arg Phe His Asn Gln Ser Glu Leu Lys Asp Phe Gly Thr Glu
145                 150                 155                 160

Ala Ala Arg Pro Gln Lys Gly Arg Lys Pro Arg Pro Arg Ala Arg Ser
                165                 170                 175

Ala Lys Ala Asn Gln Ala Glu Leu Glu Asn Ala Tyr
            180                 185

<210> SEQ ID NO 23
<211> LENGTH: 9
<212> TYPE: PRT
<213> ORGANISM: Mus sp.

<400> SEQUENCE: 23

Ile Ile Tyr His Met Asp Glu Glu Glu
1               5

<210> SEQ ID NO 24
<211> LENGTH: 12
<212> TYPE: PRT
<213> ORGANISM: Mus sp.

<400> SEQUENCE: 24

Asp Asn Tyr Gln Pro Tyr Pro Cys Ala Glu Asp Glu
1               5                   10

<210> SEQ ID NO 25
<211> LENGTH: 11
<212> TYPE: PRT
<213> ORGANISM: Mus sp.

<400> SEQUENCE: 25

Ala Ile Ala Ile Asp Tyr Asp Pro Leu Glu Gly
1               5                   10

<210> SEQ ID NO 26
<211> LENGTH: 16
<212> TYPE: PRT
<213> ORGANISM: Mus sp.

<400> SEQUENCE: 26

Pro His Ser Gln Tyr Leu Ser Ala Glu Asp Ser Cys Pro Pro Ser Pro
1               5                   10                  15

<210> SEQ ID NO 27
<211> LENGTH: 4
<212> TYPE: PRT
<213> ORGANISM: Unknown
<220> FEATURE:
<223> OTHER INFORMATION: Description of Unknown: YWTD domain peptide

<400> SEQUENCE: 27

Tyr Trp Thr Asp
1
```

ANTIBODIES SPECIFIC FOR SULFATION SITES OF SCLEROSTIN

CROSS-REFERENCE TO RELATED APPLICATION

This application is a continuation of U.S. patent application Ser. No. 13/088,059, filed Apr. 15, 2011, which is a continuation-in-part of prior application Ser. No. 12/802,447, filed Jun. 7, 2010, both of which are herein incorporated in their entireties.

FIELD OF THE INVENTION

This invention relates to the field of immunotherapy, the discovery and application of pharmacological agents, and to the diagnosis and treatment of Wnt-related disorders.

BACKGROUND OF THE INVENTION (1) Field of the Invention

The present application generally relates to manipulation of signal transduction proteins. More specifically, the invention is directed to sulfated Wnt pathway proteins and the manipulation of those proteins for research, diagnostic and therapeutic purposes (2) Description of the Related Art As used herein and in parent U.S. patent application Ser. No. 12/802,447, "sulfation" or "sulfonation" is the post-translational addition of a sulfate moiety to a protein.

Although the nature of a protein is dictated primarily by the particular amino acid sequences derived from transcription of its nucleic acid coding sequence, there are post-transcriptional processes that may also affect its properties. Some of these modifications are large scale rearrangements such as: (a) conversion of an inactive pro-enzyme into an active form by removal of part of an amino acid sequence; (b) protease digestion of a composite protein into individual segments with varied functions as seen in some viral proteins (for instance, the polyprotein of HIV); or (c) removal of an internal amino acid sequence (an intein) by protein splicing. In addition to these cleavage processes, modification of individual amino acids can take place by enzymatic addition of functional groups such as methyl, acetyl, phosphate, glycosyl, palmitoyl, sulfate and ubiquitin groups.

The difference in functionality caused by these modifications can induce radical differences in properties. For example, proinsulin is an inactive enzyme that is only found in its active form (insulin) after proteolytic cleavage transforms the protein into separate peptide chains connected by disulfide bonds. In another instance, the addition of a ubiquitin moiety does not necessarily affect its enzymatic functions but generates a signal for degradation of the "tagged" protein. Even relatively modest alterations, such as acetylation and phosphorylation of one or more amino acids in a protein, can induce remarkable changes in the properties of a protein target. The importance of both of these processes in controlling levels of activities within cells by such modifications can be seen by the abundance of substrate specific versions of each of these family of proteins (acetylases and kinases) within a cell. Further control is exerted by the action of proteins that reverse these changes, i.e., de-acetylases and phosphatases. These modifications can result in an increase or a decrease in the activity level of the target protein and/or a change in its physical locale.

Although the kinase and acetylase modifications are well known areas of research, the importance of sulfation is receiving increased attention. For recent reviews see Stone et al., 2009 New Biotechnology 25:299-317 and Monigatti et al., 2006 Biochim Biophys Acta 1764:1904-1913. Sulfation of tyrosines is believed to take place in about 1% of the tyrosines in proteins and appears to facilitate protein-protein interactions (Baeuerle and Huttner 1985 JBC 260:6434-6439, Kehoe and Bertozzi 2000 Chem Biol 7:R57-R61). Of particular interest is the connection between sulfation with receptors and their ligands, since the enzymes responsible for sulfation, tyrosylprotein sulfotransferase-1 (TPST1) and TPST2, are localized in the Golgi apparatus. Although sulfation has been mostly studied in cytokine receptors and their ligands, it has been recently noted that unsulfated Wnt does not generate as strong a signal as sulfated Wnt, presumably due to a differential ability of the unsulfated ligands to bind the LRP5/6 receptors that are involved in the Wnt signaling system (Cha et al., 2009 Current Biol 19:1573-1580). In addition to tyrosine, evidence has become available that serine and threonine are also potential sites, although at the present time it is not known if this is carried out by the same enzymes that modify tyrosines (TPST-1 and TPST-2) or if another enzyme or enzymes are responsible (Medzihradszky et al., 2004 Molec Cell Proteomics 3:429-440). The increased binding of sulfated proteins for their binding partner is, at least in some cases, due to the formation of a salt bridge between the sulfate group and arginine residues on the binding (see Woods et al., 2007, J. Proteome Res. 6:1176-1182 and references cited therein).

Testing for the presence of sulfation modifications in a protein can be carried out using various methods (for reviews, see Monigatti et al. 2006, Stone et al. 2009, and Seibert and Sakmar 2007 Polymer 90:459-477). The two most popular methods for this type of analysis is the use of mass spectrometry (MS), or antibodies that are specific for Sulfo-Tyr. With regard, to mass spectrometry, definitive answers on the presence of sulfated tyrosines can be achieved, but due to the lability of the bond between the sulfate group and tyrosine, special modifications have to be made to the standard mass spectrometry protocols (Drake and Hortin, 2010 Int J Biochem Cell Biol 42:174-179). In a more biological approach, antibodies have been developed that can detect the presence of sulfated tyrosine residues. Antibodies have been developed that can detect the presence of sulfated tyrosines regardless of the particular peptide sequence they are embedded within (Kehoe et al., 2006 Molec Cell Proteomics 5:2350-2363; Hoffhines et al., 2006 J. Biol Chem 281:37,877-37,887). The general nature of their recognition allows a wide variety of different proteins to be identified as long as they contain a sulfated tyrosine. In many cases, proteins have to be isolated or separated for this type of analysis to observe individual effects, since there is no discrimination between the different sulfated proteins by such antibodies. For instance, the extent of sulfation can be determined for individual isolated proteins of interest or patterns of a group of proteins can be analyzed. In an alternative approach, antibodies have been developed for specific proteins with a sulfated tyrosine. These antibodies can detect differences between sulfated and non-sulfated forms and can identify the presence of the sulfated protein in a mixture of other proteins (Bundgaard et al., 2008 Methods Mol Bio 446:47-66). The specificity of the epitope requires that a new antibody has to be developed for each particular protein of interest.

As information has accumulated concerning the amino acid sequences that are used as substrates for sulfation, it has become clear that there is no simple consistent recognition sequence (see, e.g., Niehrs et al., 1990 JBC 265:8525-8532, Bundgaard et al., 1997 JBC 272:31,700-31,705). A computer program called "Sulfinator" has been created recently that is capable of analyzing protein sequences and predicting the presence or absence of sulfation sites (Monigatti et al. 2002 Bioinformatics 18:769-770). The program achieves its highest accuracy only when proteins are tested that are either receptors, or ligands for receptors, because these are proteins that are processed through the Golgi apparatus where the TPST-1 and TPST-2 enzymes are localized. Proteins that are cytosolic in nature are physiologically irrelevant since even if they have appropriate sequences they would never come into contact with the tyrosine sulfotransferases. The Sulfinator does not detect the extent of sulfation.

In detecting the extent of sulfation, experiments have shown that even proteins that are substrates for sulfation do not always represent a homogeneous population with complete sulfation. For example, gastrin peptides, which are easily sulfated, show a mixed population of both sulfated and unsulfated forms in roughly equal proportions (Hilsted and Rehnfeld 1987 JBC 262:16,953-16,957). In another instance, there may be tissue specific differentiation on the extent of tyrosine sulfation of Chromogranin A that depends upon whether it is made in parathyroid or adrenal cells (Gorr and Cohn, 1999, JBC 265:3012-3016). Different effects have also been observed for proteins such as gastrin/cholecystokinin peptides and their precursors where varying degrees of modification are seen during ontogenesis and pathogenesis of certain diseases (Rehfeld et al., 1989 Biochimie 70:25-31). Furthermore, in certain circumstances, such as in the expression of cloned recombinant proteins, there may be undersulfation of proteins that would otherwise be completely modified (Seibert and Sakmar 2008 Biopolymers 90:459-477).

Although extensive efforts have been made in searching for pharmaceutical agents that affect kinase activity, compounds that affect sulfation modifications have only recently attracted attention (see, e.g., Hemmerich et al., 2004 Drug Discovery Today 9:967-975). The potential utility of influencing sulfation reactions can be seen, however, by recent discoveries that CCR5, one of the receptors for recognition of HIV, is sulfated. The importance of this modification can be seen by results with chlorate (an inhibitor of tyrosine sulfation), where the presence of this factor decreases the affinity of gp120/CD4 complexes toward the CCR5 receptor (Farzan et al., 1999 Cell 96:667-676). Although there are instances where the presence of a sulfation modification enhances binding, there are also numerous instances where there is an absolute requirement for sulfation to take place in order for certain proteins to have biological activity (Farzan et al., 2001 J Exp Med 193:1059-1065; Costaglia et al. 2002 EMBO J 21:504-513; Gao et al., 2003 JBC 278:37902-37908; Gutierrez et al., 2004 JBC 279:14726-14733; Hirata et al., 2004 JBC 279:51775-51782, Fieger et al., 2005 FASEB J 19:1926-1928 and Colvin et al., 2006 Molec Cell Biol 26:5838-5849).

Furthermore, in vitro studies also show the importance of sulfation with regard to binding of gp120/CD4 complexes with CCR5 peptides (Cormier et al., 2000 Proc. Nat. Acad. Sci USA 97:5762-5767). As such, it has been recognized that the disruption of the sulfation of CCR5 may be a treatment for HIV infection and disease processes. In another example, Liu et al. 2008 (Am J Resp Cell Molec Biol 38:738-743) hypothesized that sulfation was a general feature of cytokine receptors and found that at least 10 different cytokine receptors that are involved in asthma and chronic obstructive pulmonary disease (COPD) are sulfated. On this basis, the authors concluded that incorporation of this discovery into the structural design of receptor antagonists might show value in the development of effective drug therapies for asthma, COPD and similar inflammatory lung diseases.

Changes in sulfation patterns have also been found for tumor derived enzymes (Itkonen et al., 2007 FEBS Journal 275:289-301 and a dependency on sulfation has been shown for binding of P-selectin to cancer cells (Ma and Geng 2002 J Immunol 168:1690-1696) and tumorigenesis (Feng et al., 2010 J Vir 84:3351-3361).

SUMMARY OF THE INVENTION

The present invention is based in part on the discovery that several Wnt pathway proteins, including Sclerostin, Disheveled1 (Dvl1), Dickkopf1 (Dkk1), Kremen1 (Kr1), Frizzled6 (Fz6) and LRP5, are post-translationally sulfated, where the sulfated protein is expected to have tighter binding characteristics to ligands interacting therewith than the unsulfated counterpart. This discovery enables the use of various therapeutic, diagnostic and research methods and compositions.

Thus, in some embodiments, provided is a protein comprising an antibody binding site that binds to a sulfated epitope of a Wnt pathway protein that is not Wnt5A, Wnt11, Wnt3a or sFRP-1.

In other embodiments, a composition comprising an isolated and purified Wnt pathway protein is provided. In these embodiments, the protein is sulfated but not glycosylated.

Additionally provided is a preparation of an isolated and purified Wnt pathway protein comprising a sulfation site, wherein all of the Wnt pathway protein is glycosylated but not sulfated.

Also provided is a composition comprising a peptide less than 75 amino acids long. In these embodiments, the peptide consists of a fragment of a Wnt pathway protein. The fragment in these embodiments is sulfated.

In additional embodiments, a modified Wnt pathway protein comprising a sulfation site that is not present in the native Wnt pathway protein is provided.

Further, a modified Wnt pathway protein lacking a sulfation site that is present in the native Wnt pathway protein is provided.

Also provided is a method of detecting or quantifying a sulfated Wnt pathway protein in a preparation. The method comprises combining the preparation with the above-described protein comprising an antibody binding site under conditions allowing binding of the protein comprising an antibody binding site to the sulfated Wnt pathway protein in the preparation, then determining whether the protein comprising an antibody binding site is specifically bound to the sulfated Wnt pathway protein in the preparation.

Additionally, a method of treating a subject having a disease exacerbated by Wnt activation is provided. The method comprises obtaining a Wnt pathway protein that inhibits Wnt activation and comprises a sulfation site; treating the Wnt pathway protein with a sulfotransferase that causes sulfation of the Wnt pathway protein; and administering the treated Wnt pathway protein to the subject.

Further provided is another method of treating a subject having a disease exacerbated by Wnt activation. This method comprises obtaining the above-described composition comprising a peptide, where the Wnt pathway protein inhibits Wnt activation, and administering the composition to the subject.

Additionally provided is a method of treating a subject having a disease exacerbated by Wnt inhibition. In these embodiments, the method comprises treating the subject with the protein of comprising an antibody binding site described above, wherein the Wnt pathway protein enhances Wnt inhibition.

BRIEF DESCRIPTION OF THE FIGURES

FIG. 4 is a comparison between epitopes defined by Sulfation sites of Sclerostin and epitopes previously described in the literature.

DETAILED DESCRIPTION OF THE INVENTION

Figure 1:
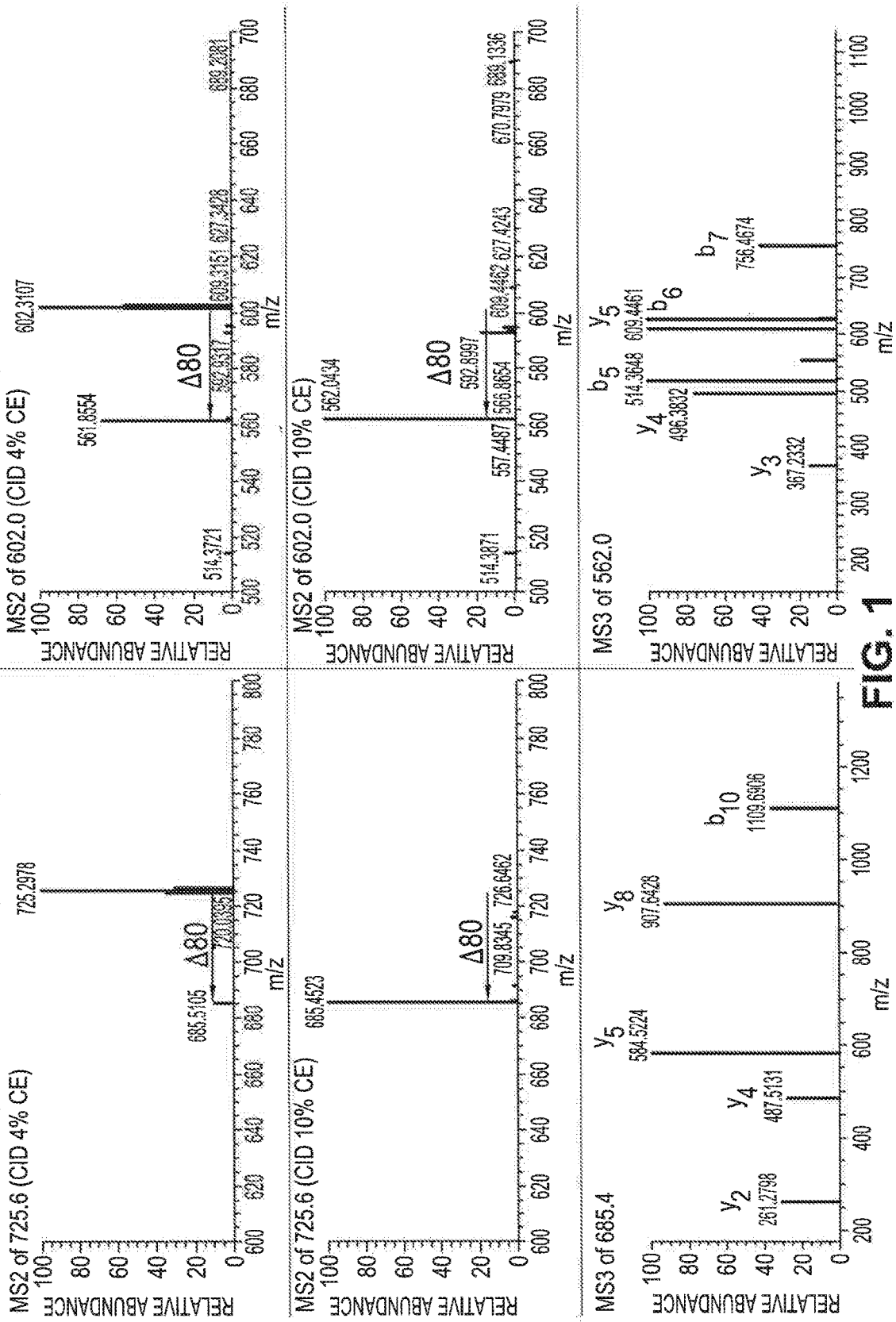
FIG. 1 shows the identification of sulfated tyrosines in Sclerostin by mass spectrometry.

As used herein, the singular forms "a", "an" and "the" are intended to include the plural forms as well, unless the context clearly indicates otherwise. Additionally, the use of "or" is intended to include "and/or", unless the context clearly indicates otherwise.

The present invention is based in part on the discovery that several Wnt pathway proteins, including Sclerostin, Disheveled1 (Dvl1), Dickkopf1 (Dkk1), Kremen1 (Kr1), Frizzled6 (Fz6) and LRP5. Previously, only Wnt11, Wnt5a, Wnt3a and sFRP-1 were identified as Wnt pathway proteins that are sulfated (Cha et al., 2009, Curr. Biol. 19:1573-1580; Zhong et al., 2007, J. Biol. Chem. 282:20523-20533). As further elaborated below, the discovery of the sulfation of additional Wnt pathway proteins enables the use of various therapeutic, diagnostic and research methods and compositions.

Sclerostin, a ligand of various LRP receptors, can be sulfated in at least two different sites, $Tyr_{43}$ and $Tyr_{213}$ (using the UniProtKB Accession No. Q9BQB4 of unprocessed Sclerostin as reference points). As shown in the Examples below, ex vivo sulfation treatment of a preparation of recombinant Sclerostin results in an increase in the affinity of the Sclerostin to the LRP5/6 receptor, as well as an increase in its ability to suppress Wnt induced expression of alkaline phosphatase.

Various means may be employed to determine the presence of sulfation modifications in proteins of interest. As described in Example 2 below, mass spectrometry (MS) analysis was carried out using Sclerostin that was expressed in mammalian cells that are capable of carrying out post-synthetic modifications such as sulfation. It should be noted that the standard conditions that are usually employed in MS studies leads to a rapid loss of sulfate groups. As such, when detection of sulfated targets is desired, avoidance of acidic conditions and lower energy inputs are required in order to increase the sensitivity of detection of sulfated tyrosines in specimens of interest (Drake and Hortin, 2010). This type of analysis may lead to the identification of the presence of sulfated tyrosines and, in many cases, the exact position of the sulfated amino acid. A caveat to be considered is that the simultaneous presence of both sulfated and unsulfated tyrosines for a given fragment does not give any estimate for their relative proportions prior to analysis since the process is still liable to losses of sulfate moieties, thereby generating some unsulfated tyrosines de novo. Distinguishing between pre-existing and converted unsulfated tyrosines is problematic and as such, MS serves best as a qualitative tool for whether sulfation occurs at all at a given site.

Prior to carrying out the MS analysis, some of the Sclerostin was used in a reaction with TPST-1 (Example 1) such that if any tyrosine modification sites were present in the sample they could be converted into a modified from. As described in the MS analysis provided in Example 2, the presence of sulfation modifications was found in both the treated and untreated samples of Sclerostin, indicating that the recombinant Sclerostin being tested had undergone sulfation modifications prior to secretion from the cells used for recombinant expression. As noted above, however, the MS analysis can determine the presence of sulfation modifications, but is unable to provide information on whether there is complete or partial modification on the sulfation sites. A protein having the appropriate sulfation sequence may be a candidate for post-synthetic modification as it passes through the Golgi apparatus prior to secretion outside of a cell, but recombinant expression systems are essentially abnormal states and there may be undersulfation of sites that normally would be fully converted. In addition, there may be differences in recognition and/or efficiency when mammalian proteins are expressed in non-mammalian systems such as insect cells.

Figure 2:
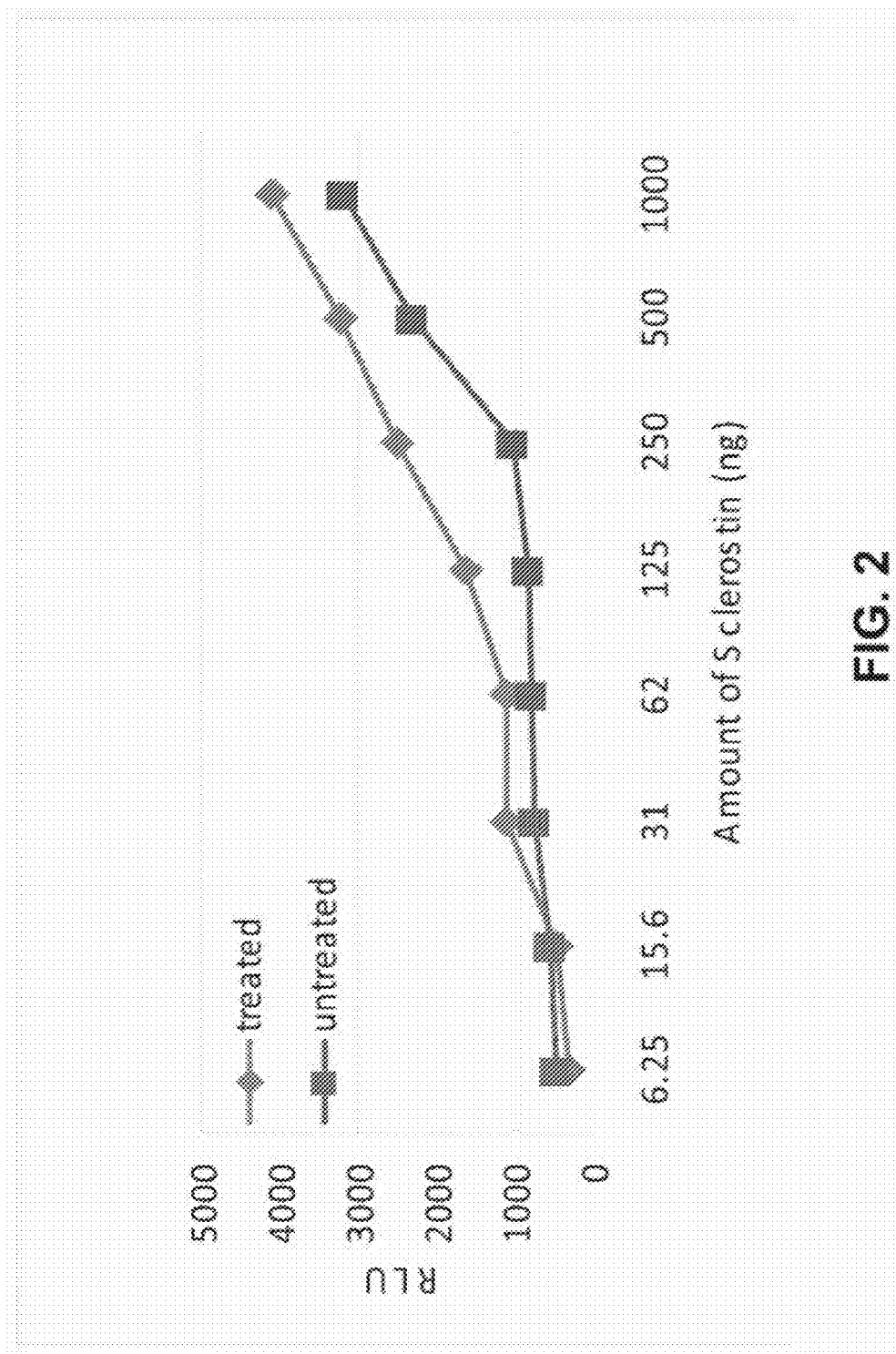
FIG. 2 are results of treatment of Sclerostin with TPST-1 and a subsequent comparison between treated and untreated Sclerostin with regard to binding to the LRP5 receptor.
Figure 3:
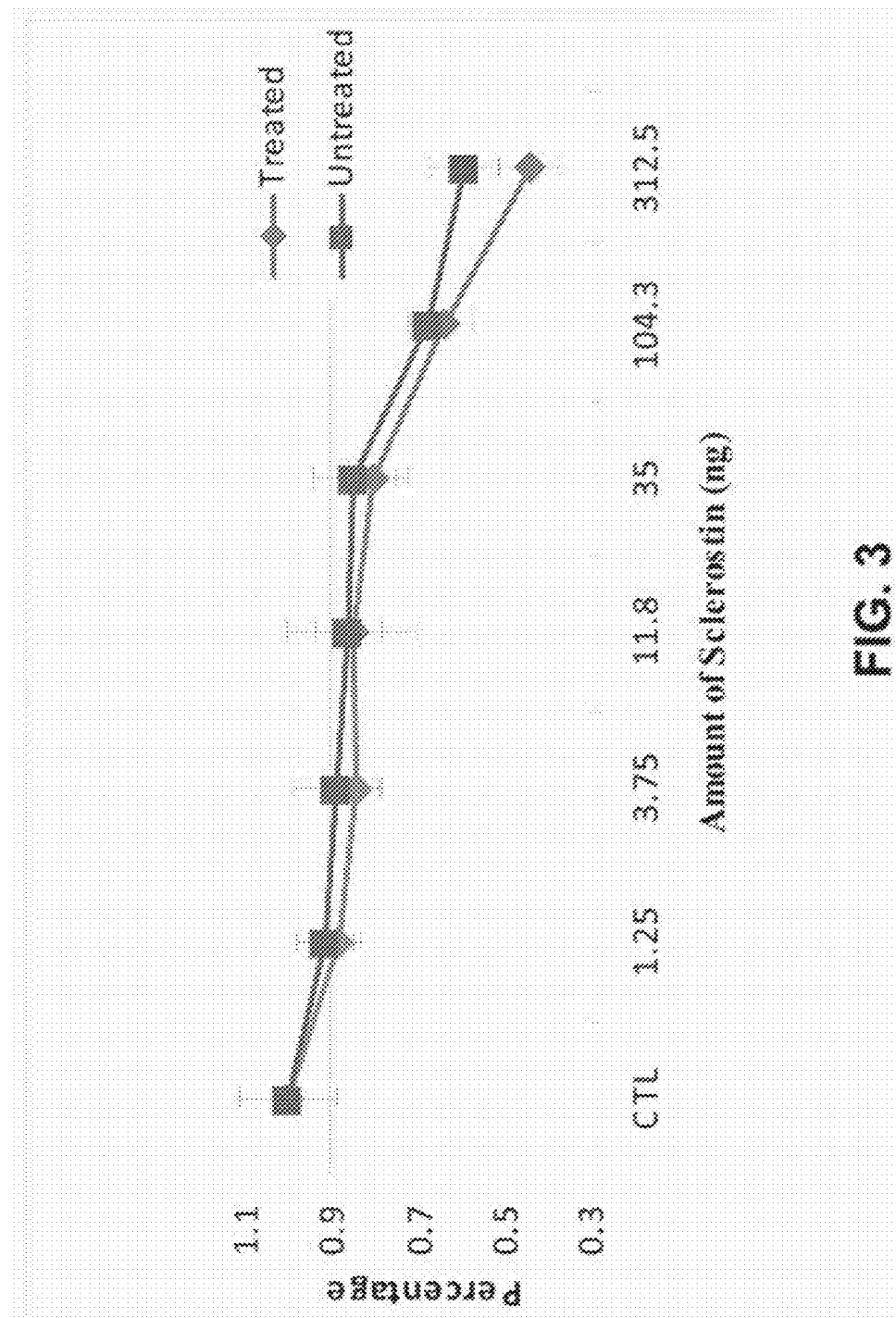
FIG. 3 shows the differential effects produced by treated and untreated Sclerostin with regard to Wnt-induced Alkaline Phosphatase expression.

As such, treated and untreated Sclerostin was used in biological assays to investigate whether there were any differences in the properties of Sclerostin after an in vitro treatment. As described in Example 3 and as shown in FIGS. 2 and 3, the differences seen with the in vitro treatment are consistent with a conclusion that some tyrosines in the sulfation sites of the recombinant Sclerostin were not sulfated prior to secretion from cells, thereby making them available for in vitro sulfation. The fully sulfated Sclerostins displayed an increased affinity for their binding partners, i.e., the original sample contains partially sulfated Sclerostin and the treated sample has an increased level of sulfation. This effect could likely be seen more dramatically if conditions were used such that a comparison was made with starting material that was completely or mostly lacking in sulfation modifications prior to an in vitro reaction. Ways that this could be accomplished are the use of yeast or bacterial expression systems, treatment of recombinant expression cells with chlorate prior to harvesting the protein, or expression in cells that have been mutated to eliminate TPST activity, such as those described by Westmuckett et al., 2008, Gen. Compar. Endocrine 156:145-153. With regard to the chlorate treatment, it has been previously shown that such treatment can strongly reduce the degree of sulfation in cells (Baeuerle and Huttner 186 BBRC 141:870-877; Hortin et al., 1988 BBRC 150:342-348; Mintz et al., 1994 J Biol Chem 269:4845-4852) and a bacterial or yeast host would lack any sulfation since they intrinsically lack the sulfotransferases responsible for tyrosine sulfation (Kehoe and Bertozii 2007 Chemistry & Biology 7:R57-R61). In addition to chlorate, sulfotransferase activity can be inhibited by sphingosine (Kasinathan et al., 1993, Biochemistry 32:1194-1198), sulfate analogs that inhibit ATP-sulfurylase, or selenite (Stone et al., 2009, New Biotechnol. 25:299-317). Conversely, if desired, sulfotransferases can be enhanced by sofalcone (Kasinathan et al., 1994, Gen. Pharmacol. 25:1017-1020.

A further method of investigation is the use of a software program called Sulfinator that can predict the presence of a sulfation site with 98% accuracy from the amino acid sequence alone (Stone et al., 2009 New Biotechnology 25:299-317). When the sequences from Sclerostin were analyzed with this program, it successfully identified the amino terminal modification of Sclerostin at $Tyr_{43}$ detected by MS analysis but missed the carboxy terminal modification at $Tyr_{213}$. This failure in Sulfinator predictability is likely due to the tyrosine in Sclerostin that is modified at the carboxy end of Sclerostin being the terminal amino acid itself; since the Sulfinator program uses the neighboring sequences surrounding a tyrosine for evaluating its likelihood of being sulfated, and by definition, a terminal tyrosine of Sclerostin would intrinsically lack sequences on one side. It should be pointed out that although the presence of a site predicted to be a sulfation site is likely dependable, there are incidents where sulfation modifications were unrecognized by the Sulfinator program but later identified in physical studies (Onnerfjord et al., 2004 JBC 279:26-33, Hoffhines et al., 2006 JBC 281:37877-37887). Nonetheless, the recognition of the $Tyr_{43}$ modification by the Sulfinator program is an independent confirmation of the sulfation of this particular amino acid in Sclerostin.

It should be understood that although sulfated tyrosines have been observed in many secreted ligands and their receptors, their presence is not necessarily required and it is inappropriate to make any predictions about their presence in the absence of any investigational analysis. As noted above, it has been estimated that ~1% of the tyrosines in cellular proteins are modified tyrosines (Huttner 1984 Methods Enzymol 107:200-223) which in turn has the implication that ~99% of them would not have this modification.

As shown in Example 9, the use of the Sulfinator program resulted in positive predictions of a sulfonation site in Dvl1 but not in Dvl2. However, since the Dishevelled protein is an intracellular protein, it may not come into contact with the Golgi apparatus and the in vivo significance of the site in Dvl 1 is not readily apparent. However, it does show that not every protein that is tested with the Sulfinator program automatically comes up with a positive result.

The same phenomenon is seen with regard to the Dkk family. Although all 4 members were tested, the presence of a sulfonation site was predicted to only be present in human and mouse Dkk1 while neither human nor mouse Dkk2, Dkk3 or Dkk4 were predicted to have sulfation sites. The presence of such a site in Dkk1 is of interest in a number of different regards. For instance, in many cases the properties of Dkk1 seems to be the opposite of Dkk2 and Dkk4 where intact Dkk1 is regarded as a strong repressor of Wnt induced stimulation whereas under some circumstances Dkk2 and Dkk4 can enhance Wnt induced activity. It is possible that differential sulfation may be a factor in this separation of properties. Secondly, as described with regard to the sulfation site in Sclerostin, the discovery of the presence of a sulfation moiety in Dkk1 implies that a virtual screening program that employs the structure of Dkk1 may be made more accurate by including the influence of the sulfation modification when predicting binding affinities of small molecules to Dkk1. Lastly, the presence of the sulfation modification endows Dkk1 with a previously unknown epitope that may be used in conjunction with an antibody that binds to the sulfation site.

A number of different members of the Frizzled family were also tested with the Sulfinator program including Fz1, Fz2, Fz3, Fz4, Fz5, Fz6, Fz7m Fz8, Fz9 and Fz10 proteins. The results of these tests were a lack of identification of a predicted sulfation site in the majority of these Frizzled proteins even though they are large transmembrane proteins with numerous tyrosines present. In the few instances where potential sulfation sites were identified, they were only on the intracellular portion and not involved in extracellular protein/protein interactions.

Also tested were LRP5, LRP6 and LRP4. When human and mouse sequences were examined, Sulfinator identified a potential sulfonation site on the extracellular portion of only LRP5. For LRP 4, no sites were predicted to be present and both LRP5 and mouse LRP6 showed a potential sulfonation site being present in the intracellular portion of these receptor proteins. Although this location precludes interaction with extracellular ligands, once a ligand has been bound to a receptor, there are one or more protein/protein interactions within the cell that is part of the signal generation process and these events may potentially be influenced by the presence of a sulfation modification. The extracellular portion of LRP5 that has been identified as a sulfation site is in the second YWTD domain, a portion of the LRP5 receptor that may be involved in binding Wnt, Dkk and Sclerostin ligands. The influence of a sulfation modification is of value in carrying out virtual screening processes for the interaction of the second YWTD domain with small molecules that affect protein/protein interactions at this site. It also has value in identifying molecules that may discriminate between the two closely related LRP5 and LRP6 receptors.

The discovery that Wnt pathway proteins, i.e., proteins that participate in the Wnt signaling system, have sulfated amino acids offers unique methods of analysis as well as therapeutic means. As described in various patent applications (e.g., U.S. patent publications 2005/0196349; 2006/0030523; 2008/0119402, hereby incorporated by reference), compounds that block the interaction between LRP5/6 receptors and the soluble ligands Dkk and Sclerostin can offer a variety of useful therapeutic means. Since it has now been discovered that the amino acid sequence of several Wnt pathway proteins can also comprise a post-synthetic sulfation modification, compounds that have been previously tested for effects on Sclerostin and Dkk with regard to Wnt signaling may be retested using separate reaction mixtures or binding assays where either the modified or unmodified versions of these proteins are tested separately. As has been pointed out earlier, some proteins exist as a mixture of sulfated and unsulfated forms and previous experiments may have been based upon such a mixture, without recognition that the net effects might be a composite of the individual effects on modified and unmodified Wnt pathway proteins. Control over the particular form (sulfated or unsulfated) of the proteins will now allow investigation into whether compounds are more or less effective with regard to using sulfated or unsulfated versions of the proteins in assays. The lack of recognition of the potential presence of a mixture of different forms also allows for the possibility that some effective compounds may have been missed due to the use of protein preparations that had a preponderance of one form over another.

Furthermore, the presence of a site that is involved in protein-protein interactions is in itself a potential therapeutic target. Thus, a series of compounds can be surveyed to see if they specifically interrupt in vitro or in vivo sulfate modification of the tyrosines in the proteins. Such pharmaceutical agents would have the potential for modifying the level of activity induced by the protein by controlling the degree of sulfation and thereby their affinity in protein-protein interactions. Pharmaceutical reagents that may be used to disrupt sulfation processes can include but not be limited to small molecules, peptides, organic molecules, cyclic molecules, heterocyclic molecules, lipids, charged lipids, glycolipids, polar lipids, non-polar lipids and aptamers. The compounds may be ones that have been designed to bind to the surface of the protein through a virtual screening process as described for Sclerostin in US Patent Publication 2005/0196349. In this process, a revised virtual structure of the protein may be devised to takes into consideration the presence of the sulfation of amino acids. Contrariwise, compounds may be tested independently from virtual screening and tested strictly on a random basis or they may be selected to have a physical resemblance to compounds that result from virtual screening processes. Such a process can also include the use of mutational substitutions at the modification sites (see, for instance, U.S. Patent Publication 2005/0196349). Thus, a series of (selected or random) compounds may be assayed for an ability to eliminate or reduce sulfation of the protein, by any means that have previously been described for analysis and/or detection of sulfation of proteins. As a control, one or more proteins that also have sulfation sites may be included to insure that the blockage of sulfation is specific for the target of interest. Any means that have been described in the past for detection of the presence of sulfated tyrosines may be used in this aspect of the present invention, thus for example, these means may be as complex as carrying out MS analysis to simpler methods such as incorporation of $^{35}S$ PAPS by TPST, immunoassays that use antibodies that recognize proteins with sulfated tyrosines irrespective of their context (Kehoe et al., 2006 and Hoffhiner et al., 2006, J Biol Chem. 281:37877-87), or antibodies that are specific for the sulfated or unsulfated forms of the protein (as will be discussed in more detail below). If desired, truncated versions of the protein that comprise the target area of interest may also be used as substrates in assays as long as their biological structures/functions are similar to the parent protein. In addition, peptides that may represent the sulfation site of the protein may also be used.

Investigations into compounds that might interrupt sulfation of proteins has been previously described by Hortin et al., 1988 BBRC 150:342-348 where compounds were found that were non-specific in that they inhibited sulfation of proteins, oligosaccharides and proteoglycans (although with varying efficiencies). A similar study has been done more recently by Kehoe et al., 2002 (Bioorg Med Chem Letters 12:129-132) where two compounds were identified that inhibited sulfation by TPST-2. Similar to the results published earlier by Hortin et al., further testing showed that the inhibitors affected other sulfotransferases as well. Even if these inhibitors only affected the TPST reaction itself, however, this approach would indiscriminately block sulfation of a wide variety of different protein targets and thereby lead to potentially toxic effects. It should be noted that knockout mice lacking either TPST-1 (Ouyang et al., 2002 JBC 277:23,731-23,787) or TPST-2 (Borghei et al., JBC 281: 9423-9431) activity are essentially viable but exhibit a variety of pleiotropic defects. Partial overlap in the functionality of the two TPST enzymes can be seen by experiments with a double knockout that is missing both TPST-1 and TPST-2 where most progeny died soon after birth and any survivors failed to thrive (Westmuckett et al., 2008). These double knockouts exemplify a situation that may be more akin to the presence of a general TPST inhibitor. In addition, as noted previously, there are many proteins involved in protein-protein interactions where sulfation is obligatory for biological activity and some are involved in inflammatory responses that require sulfation for functionality; as such, it may be that the double knockouts are phenotypically silent except under certain conditions where such responses would be induced or required. Targeting the modification of a particular sulfation target as described in the present invention is likely to be superior to efforts to block sulfation in general since it is likely to have more specific effects than a general blockage that may produce deleterious as well as beneficial effects.

As indicated above, prokaryotic expression systems lack the ability to post-translationally modify proteins expressed therein. As such, a Wnt pathway protein having a sulfation site, when recombinantly expressed in prokaryotes such as bacteria (e.g., E. coli) are not sulfated or glycosylated, even though such proteins are sulfated and glycosylated when expressed naturally or in eukaryotic expression systems. Thus, if a Wnt pathway protein having a sulfation site is expressed in a prokaryotic system to achieve the high yields that can be obtained from such expression systems, the protein will not be sulfated or glycosylated. Such a protein can then be sulfated, e.g., by using TPST, to obtain in high yield a Wnt pathway protein that is sulfated but not glycosylated. The TPST treatment can be achieved in vitro or in a cell expressing a TPST, either as a native enzyme or produced recombinantly.

Thus, provided herein is a composition comprising an isolated and purified Wnt pathway protein, where the protein is sulfated but not glycosylated. In various embodiments, the protein is sulfated on a tyrosine. The Wnt pathway protein in these embodiments can be from any source, for example an insect (e.g., a Drosophila), an amphibian (e.g., a Xenopus), or a mammal (e.g., a rodent or human).

In some embodiments, the Wnt pathway protein is sulfated at a native sulfation site. As used herein, a "native sulfation site" is an amino acid sequence of a protein that would ordinarily be sulfated when expressed in a cell where the protein would normally be found. Here, the Wnt pathway protein can be any protein that has a native sulfation site, e.g., a Wnt, for example Wnt5A, Wnt11, Wnt3a or another Wnt having a native sulfation site. The protein can also be, e.g., a Sclerostin, a Dvl1, a Dkk1, a Kr1, a Fz6, an LRP5, or any other Wnt pathway protein now known or later discovered that comprises a native sulfation site. Where the protein is a Sclerostin, in various embodiments the protein is sulfated on the tyrosine equivalent to the $Tyr_{213}$ of human Sclerostin (i.e., the corresponding position when the Sclerostin is not human Sclerostin. Where the protein is a Dvl1, the protein in various embodiments is sulfated on the tyrosine equivalent to the $Tyr_8$ of human Dvl1. Where the protein is Dkk1, in various embodiments the protein is sulfated on the tyrosine equivalent to the $Tyr_{83}$ of human Dkk1. Where the protein is a Kr1, in various embodiments the protein is sulfated on the tyrosine equivalent to the $Tyr_{175}$ or the $Tyr_{178}$ of human Kr1. Where the protein is Fz6, in various embodiments, the protein is sulfated on the tyrosine equivalent to the $Tyr_{580}$ of human Fz6. Where the protein is LRP5, in various embodiments the protein is sulfated on the tyrosine equivalent to the $Tyr_{380}$ or the $Tyr_{1583}$ of human LRP5.

In other embodiments, the protein is sulfated at a sulfation site that is not native to the protein. Such a sulfation site can be added to the native protein by any means, including by recombinant DNA methods, or by chemical methods. In various embodiments, the sulfation site comprises a tyrosine that is not native to the protein. In other embodiments, the tyrosine is native to the protein but surrounding amino acids are modified to engineer a sulfation site that is recognized by a sulfotransferase, e.g., a TPST enzyme. The protein of these embodiments can be any protein in the Wnt pathway, including a Wnt, a Dvl2, a Dvl3, a Dkk2, a DKK3, a DKK4, a Kr2, a Fz1, a Fz2, a Fz3, a Fz4, a Fz5, a Fz7, a Fz8, a Fz9, a Fz10, an LRP4, an LRP6, or any other Wnt pathway protein, including proteins that have a native sulfation site and proteins that do not have a native sulfation site, including GSK-3β, APC, β-Catenin, Axin, TCF, LEF, or any other Wnt pathway protein now known or later discovered.

It is expected that a TPST enzyme from any species would cause sulfation of a sulfation site on a protein from any species.

With the discovery disclosed herein that many Wnt pathway proteins comprise a sulfation site, and that in natural eukaryotic systems only a proportion of Wnt pathway proteins that comprise a sulfation site are actually sulfated, it becomes clear that a preparation where all the Wnt pathway proteins are either sulfated or not sulfated is desirable. Thus, where a Wnt pathway protein is prepared in a eukaryotic system, it is now clear that glycosylated protein that is a mixture of sulfated and unsulfated forms is obtained if measures are not taken to obtain only sulfated protein (for example by treating the protein with TPST) or unsulfated protein (for example by preparing the protein in cells exposed to chlorate).

Thus, provided is a preparation of a Wnt pathway protein comprising at least one sulfation site and at least one glycosylation site, where all of the Wnt pathway protein in the preparation is glycosylated but not sulfated. In some embodiments, the Wnt pathway protein does not comprise a native sulfation site, but the sulfation site is engineered into the protein, as described above. In other embodiments, the Wnt pathway protein has a native sulfation site. The preparation can be achieved by any means known in the art, for example by translating the protein in a eukaryotic cell treated with a compound that inhibits sulfation. See, e.g., Stone et al., 2009, New Biotechnol. 25:299-317. Hortin et al., 1988 BBRC 150:342-348, and Kehoe et al., 2002, Bioorg Med Chem Letters 12:129-132. In some embodiments, the compound that inhibits sulfation is chlorate. The Wnt pathway protein in these embodiments can be from any source, for example an insect (e.g., a *Drosophila*), an amphibian (e.g., a *Xenopus*), or a mammal (e.g., a rodent or human). The Wnt pathway protein in these embodiments can be any such protein that has a native sulfation site, e.g., a Wnt, for example Wnt5A, Wnt11, Wnt3a or another Wnt having a native sulfation site. The protein can also be, e.g., a Sclerostin, a Dvl1, a Dkk1, a Kr1, a Fz6, an LRP5, or any other Wnt pathway protein now known or later discovered that comprises a native sulfation site.

As indicated above, a Wnt pathway protein can be engineered to comprise a sulfation site that is not present in the native Wnt pathway protein. Such a protein would be expected to increase binding to its native binding partner if the protein is engineered such that the nonnative sulfation site mimics a sulfation site present in analogs of the Wnt pathway protein. For example, as shown in Example 9, human Dkk1 has a sulfation site comprising a tyrosine at position 83, but human Dkk2 does not comprise a sulfation site. The human Dkk2 can be engineered to have a sulfation site by modifying the region in that protein that corresponds to the region around position 83 of human Dkk1 to have the same amino acid sequence as the human Dkk1 protein (i.e., DNYQPYPCAEDE). Such a modified Dkk2 would be sulfated like Dkk1 and would be likely to have increased binding to LRP5/6 and increased Wnt inhibitory activity similar to Dkk1 (see Example 10). Similarly, a sulfation site can be engineered into a region of a Wnt pathway protein from one species by modifying a region in that protein that corresponds to a region of the homolog from another species that has a sulfation site. For example, as shown in Example 9, mouse LRP6 has a sulfation site comprising a tyrosine at position 1562, but the human LRP6 does not have a sulfation site. The human LRP6 can be engineered to modify the region around the human LRP6 corresponding to the region of the mouse LRP6 around position 1562. Such a sulfated human LRP6 would be expected to behave similar to the sulfated mouse LRP6.

Thus, the present invention provides a modified Wnt pathway protein comprising a sulfation site that is not present in the native Wnt pathway protein. The Wnt pathway protein in these embodiments can be from any source, for example an insect (e.g., a *Drosophila*), an amphibian (e.g., a *Xenopus*), or a mammal (e.g., a rodent or human). In some embodiments, the Wnt pathway protein further comprises a native sulfation site. In other embodiments, the Wnt pathway protein does not further comprise a native sulfation site. Nonlimiting examples of proteins that can be utilized in these embodiments is a Wnt, is a Sclerostin, a Dvl1, a Dkk1, a Kr1, a Fz6, an LRP5, a Dvl2, a Dvl3, a Dkk2, a DKK3, a DKK4, a Kr2, a Fz1, a Fz2, a Fz3, a Fz4, a Fz5, a Fz7, a Fz8, a Fz9, a Fz10, an LRP4, an LRP6, or any other Wnt pathway protein now known or later discovered. The protein of these embodiments can be prepared by recombinant DNA methods or by chemical methods.

Similar to the above embodiments, the present invention also provides a modified Wnt pathway protein lacking a sulfation site that is present in the native Wnt pathway protein. Such a protein is useful where reduced binding of the Wnt pathway protein is desired. These proteins can be prepared by any of a number of strategies, e.g., by engineering the protein to eliminate the tyrosine that is sulfated in the native protein, or by engineering the sulfation site to be the same as a homologous protein from a different species, or from the same family (for example by engineering the region around position 83 in human Dkk1 to have the same sequence as the analogous region of human Dkk2). These modified proteins can be prepared by recombinant methods or by chemical methods. Nonlimiting examples of proteins that can be utilized in these embodiments is a Wnt, is a Sclerostin, a Dvl1, a Dkk1, a Kr1, a Fz6, an LRP5, a Dvl2, a Dvl3, a Dkk2, a DKK3, a DKK4, a Kr2, a Fz1, a Fz2, a Fz3, a Fz4, a Fz5, a Fz7, a Fz8, a Fz9, a Fz10, an LRP4, an LRP6, or any other sulfation site-containing Wnt pathway protein now known or later discovered. The protein of these embodiments can be prepared by recombinant DNA methods or by chemical methods.

Nucleic acids comprising a nucleotide sequence encoding these modified Wnt pathway proteins is also provided, as are vectors (e.g., bacterial, yeast, mammalian, viral, expression, shuttle, plasmid, etc.) comprising the nucleic acid. Where the vector is an expression vector, the vector can further comprise control elements such that the modified protein is expressed constitutively or under the control of an inducible promoter. Prokaryotic and eukaryotic cells comprising these vectors are also envisioned. These cells and vectors can be administered or implanted into a mammal, e.g., a rodent or a human, e.g., for therapeutic purposes The identification of peptide sequences comprising a modified tyrosine also allows the use and design of artificial peptides that contain these modifications. Presumably these should have higher binding affinities than their unmodified counterparts. In this regard, it is noted that peptides comprising a sulfated tyrosine have been shown to mimic the binding of the sulfated whole protein from which it was derived. See, e.g., Farzan et al., 2001, J. Exp. Med. 193: 1059-1065. Binding of these peptides to the protein that normally interacts with the complete protein may produce a variety of effects. For instance, some of these peptides could act in a positive fashion by invoking the same response that the intact protein induces. Contrariwise, the peptide could act as a competitive inhibitor and prevent the intact protein from binding. For example, a peptide with sequences from either the carboxy or amino end could reduce the ability of Sclerostin to bind to a LRP receptor. Although the sulfated peptide would be the basis for the design, it is understood that the actual components can be artificial equivalent of these peptides. Examples of compounds made with such components can comprise but not be limited to the peptide mimetics described in pending U.S. Patent Publication 2008/0119402, as well the substitution of dextro isomers instead of the normal levo forms and peptidomimetics such as those described in Hammond et al., 2006 Chem & Biol 13:1247-1251. Other examples of analogs that may find use with the present invention are "unnatural amino acids" where in it is understood that in the context of the present invention "unnatural amino acids" refers to amino acids that are not genetically encoded, i.e., they are not represented by a nucleotide codon. This would include the dextro isomers discussed above as well as other amino acids such as Aib (amino-isobutyric acid), bAib (3-aminoisobutyric acid), Nva (norvaline), β-Ala, Aad (2-aminoadipic acid), bAad (3-aminoadipic acid), Abu (2-aminobutyric acid), Gaba (γ-aminobutyric acid), Acp (6-aminocaproic acid), Dbu (2,4-diaminobutyric acid), TMSA (trimethylsilyl-Ala), alle (allo-Isoleucine), Nle (Norleucine), tert.Leu, Cit (Citrulline), Orn, Dpm (2,2'-diaminopimelic acid), Dpr (2,3-diaminopropionic acid), α- or β-Nal, Cha (cyclohexyl-Ala), hydroxy-proline, Sar (Sarcosine) etc., cyclic amino acid units and $N^{\alpha}$-alkylated amino acid units, e.g. MeGly ($N^{\alpha}$-Methyl-glycine), EtGly ($N^{\alpha}$-ethylglycine) and EtAsn ($N^{\alpha}$-ethyl-asparagine). Accordingly, synthetic peptides can be made that include one or more of these unnatural amino acids.

Thus, further provided herein is a composition comprising a peptide less than 75 amino acids or amino acid analogs. In these embodiments, the peptide consists of a fragment of a Wnt pathway protein, where the fragment is sulfated. The peptide can be, e.g., at least 5 amino acids or amino acid analogs long, at least 10 amino acids or amino acid analogs long, at least 20 amino acids or amino acid analogs long, at least 30 amino acids or amino acid analogs long, at least 40 amino acids or amino acid analogs long, at least 50 amino acids or amino acid analogs long, at least 60 amino acids or amino acid analogs long, or at least 70 amino acids or amino acid analogs long. In some embodiments, the peptide is sulfated at a sulfation site native to the Wnt pathway protein. In other embodiments, the peptide is sulfated on an amino acid or amino acid analog that is not subjected to sulfation in the native protein. The peptides can be prepared by chemical methods. See, e.g., Seibert and Sakmar 2007, Peptide Science 90:459-477. The Wnt pathway protein from which the peptide is derived in these embodiments can be from any source, for example an insect (e.g., a Drosophila), an amphibian (e.g., a Xenopus), or a mammal (e.g., a rodent or human).

The peptide of these embodiments can be sulfated by any method now known or later discovered. For example by chemical peptide synthesis methods, or using a sulfotransferase, e.g., a TPST1 or TPST2.

The peptide can be derived from any Wnt pathway protein, for example a protein having a native sulfation site or a protein that is engineered to have such a site. Nonlimiting examples of proteins from which the peptide can be derived are a Sclerostin, a Dvl1, a Dkk1, a Kr1, a Fz6, an LRP5, a Wnt, a Dvl2, a Dvl3, a Dkk2, a DKK3, a DKK4, a Kr2, a Fz1, a Fz2, a Fz3, a Fz4, a Fz5, a Fz7, a Fz8, a Fz9, a Fz10, an LRP4, an LRP6 or any other Wnt pathway protein now known or later discovered. Where the protein is a Sclerostin, in various embodiments the peptide is sulfated on the tyrosine equivalent to the $Tyr_{213}$ of human Sclerostin. Where the protein is a Dvl1, the peptide in various embodiments is sulfated on the tyrosine equivalent to the $Tyr_8$ of human Dvl1. Where the protein is Dkk1, in various embodiments the peptide is sulfated on the tyrosine equivalent to the $Tyr_{83}$ of human Dkk1. Where the protein is a Kr1, in various embodiments the peptide is sulfated on the tyrosine equivalent to the $Tyr_{175}$ or the $Tyr_{178}$ of human Kr1. Where the protein is Fz6, in various embodiments, the peptide is sulfated on the tyrosine equivalent to the $Tyr_{580}$ of human Fz6. Where the protein is LRP5, in various embodiments the peptide is sulfated on the tyrosine equivalent to the $Tyr_{380}$ or the $Tyr_{1583}$ of human LRP5.

These embodiments also encompass analogs of the above peptides having a sequence that is altered from the native Wnt pathway protein, e.g., having one or several amino acids different from the native protein, where the altered amino acids do not affect the activity of the peptide. Identification of such analogs for any peptide derived from any Wnt pathway protein is routine in the art.

Nucleic acids comprising a nucleotide sequence encoding these peptides is also provided, as are vectors (e.g., bacterial, yeast, mammalian, viral, expression, shuttle, plasmid, etc.) comprising the nucleic acid. Where the vector is an expression vector, the vector can further comprise control elements such that the peptide is expressed constitutively or under the control of an inducible promoter. Prokaryotic and eukaryotic cells comprising these vectors are also envisioned. These cells and vectors can be administered or implanted into a mammal, e.g., a rodent or a human, e.g., for therapeutic purposes.

Additionally, although the tyrosine modifications have been discussed in terms of alterations of a protein's affinity for a binding partner in a heterodimeric interaction, dimerization is also an example of a protein/protein interaction and as such, a homodimeric protein interaction may also be influenced by sulfation modifications, and the protein itself, should be included in the potential list of binding partners for the Wnt pathway protein. The degree of dimerization may have further effects with regard to binding to other proteins, where the affinity of a dimeric protein may be higher than that of a monomeric form. For instance, see Jekel et al., Biochimica Biophica Acta 1996 1291:195-198 where the affinity of a dimerized antigenic peptide is higher than the monomeric form with regard to binding to an antibody. In another instance, TNF-α exists in trimeric form and binds to three receptors simultaneously (Banner et al., 1993, Cell, 73:431-445). Since dimerization or multimerization of proteins may be affected by sulfation processes, the methods above may also be applied to homodimeric interactions when the ability of a compound to affect sulfation is being analyzed. Assays that measure the ability of sulfated and unsulfated protein to form a complex with a binding partner may also be carried out with another molecule of the protein as the intended binding partner. Antibodies may also be developed that are specific to dimers as compared to monomers as previously described by Raven et al., in US Patent Publication 20050163776. Selectivity may be carried out by testing for the ability to react with dimers and then counter-selecting by eliminating antibodies that exhibit cross-reactivity with the monomeric form.

Another group of useful reagents provided herein are antibodies directed to the sulfation site. In the first place, the identification of the sulfation site offers evidence that the site is likely to be involved in protein-protein interactions. Thus, for instance, the particular portion of the Sclerostin protein involved in interaction with LRP5/6 has not been clearly identified, but the discovery of the sulfation site of Sclerostin in the amino terminal sequences described in Example 2 provides a novel target for antibody binding that is likely to affect the interaction of Sclerostin with LRP5/6 that is different from the Sclerostin sequences previously postulated by Ververka et al., 2009 JBC 284:10,890-10,900, Weidauer et al., 2009 BBRC 380:160-165 and Krumlauf in U.S. Pat. No. 7,585,501.

Although the sulfonation modifications are not part of the sites described above by Ververka et al., 2009 and Weidauer et al. 2009, it should be pointed out that their studies used Sclerostin prepared from *E. coli* and as such, they were studying sclerostin that lacked any post-translational modifications. This offers the possibility of increased binding that augments the binding taking place through the "core" portion of Sclerostin that they have studied. For instance, there could be intra-strand interactions of the sulfonated tyrosines at the carboxy or amino ends with the "core" portion of Sclerostin that alters the binding properties of the protein as a whole. Alternatively, binding through the "core" portion can be augmented by a separate binding of the modified tyrosines of the Sclerostin to its LRP5/6 binding partner. In either case, the overall effect is the further stabilization of the protein/binding partner complex. Of course, it is understood that other explanations are also possible for the ability of the sulfonated tyrosine(s) of sclerostin to enhance biding of sclerostin to LRRP5/6. This same rationale applies to other sulfated Wnt pathway proteins when potentially, sulfation can directly lead to an increased affinity in the core region or by an intrastrand or interstrand binding event that leads to an overall increase in complex stability.

Thus, provided is a protein comprising an antibody binding site that binds to a sulfated epitope of a Wnt pathway protein that is not Wnt5A, Wnt11, or Wnt3a. As used herein an "antibody binding site" is a portion of an immunoglobulin that binds to an antigen. The protein in these embodiments will thus bind to a sulfated epitope of the Wnt pathway protein. The protein may also take any other form that is known in the art for use in immunodetection or immunotherapy.

The proteins of these embodiments include non-immunoglobulin proteins fused, e.g., by chemical or recombinant DNA methods, to an antibody binding site. In other embodiments, the protein is an antibody or an antibody fragment. For instance, the protein may be polyclonal, monoclonal, chimeric, human, humanized, bispecific, multispecific, primatized or an antibody fragment. Antibody fragments that me be of use in the present invention may comprise but not be limited to is Fab, ScFv, Fab', F(ab')$_2$, Fv, Fv(ab)$_2$ or aggregates thereof. The antibody binding site may be derived from any vertebrate species including but not limited to mice, rabbits, goats, sheep, chickens, camels, or humans. The antibody binding site can also be from any immunoglobulin class including IgG, IgM, or IgA.

In some embodiments, the antibody binding site can distinguish between the sulfated and unsulfated sulfation site, e.g., where the antibody binding site binds to the sulfated sulfation site but does not substantially bind to the unsulfated sulfation site. In other embodiments, the antibody binding site does not distinguish between the sulfated and unsulfated forms, but are still specific for the surrounding amino acids at the Wnt pathway protein sulfation site.

The antibody binding site can be directed against any Wnt pathway protein, for example a protein having a native sulfation site or a protein that is engineered to have such a site. Nonlimiting examples of proteins from which the peptide can be derived are a Sclerostin, a Dvl1, a Dkk1, a Kr1, a Fz6, an LRP5, a Wnt, a Dvl2, a Dvl3, a Dkk2, a DKK3, a DKK4, a Kr2, a Fz1, a Fz2, a Fz3, a Fz4, a Fz5, a Fz7, a Fz8, a Fz9, a Fz10, an LRP4, an LRP6 or any other Wnt pathway protein now known or later discovered.

Figure 4:
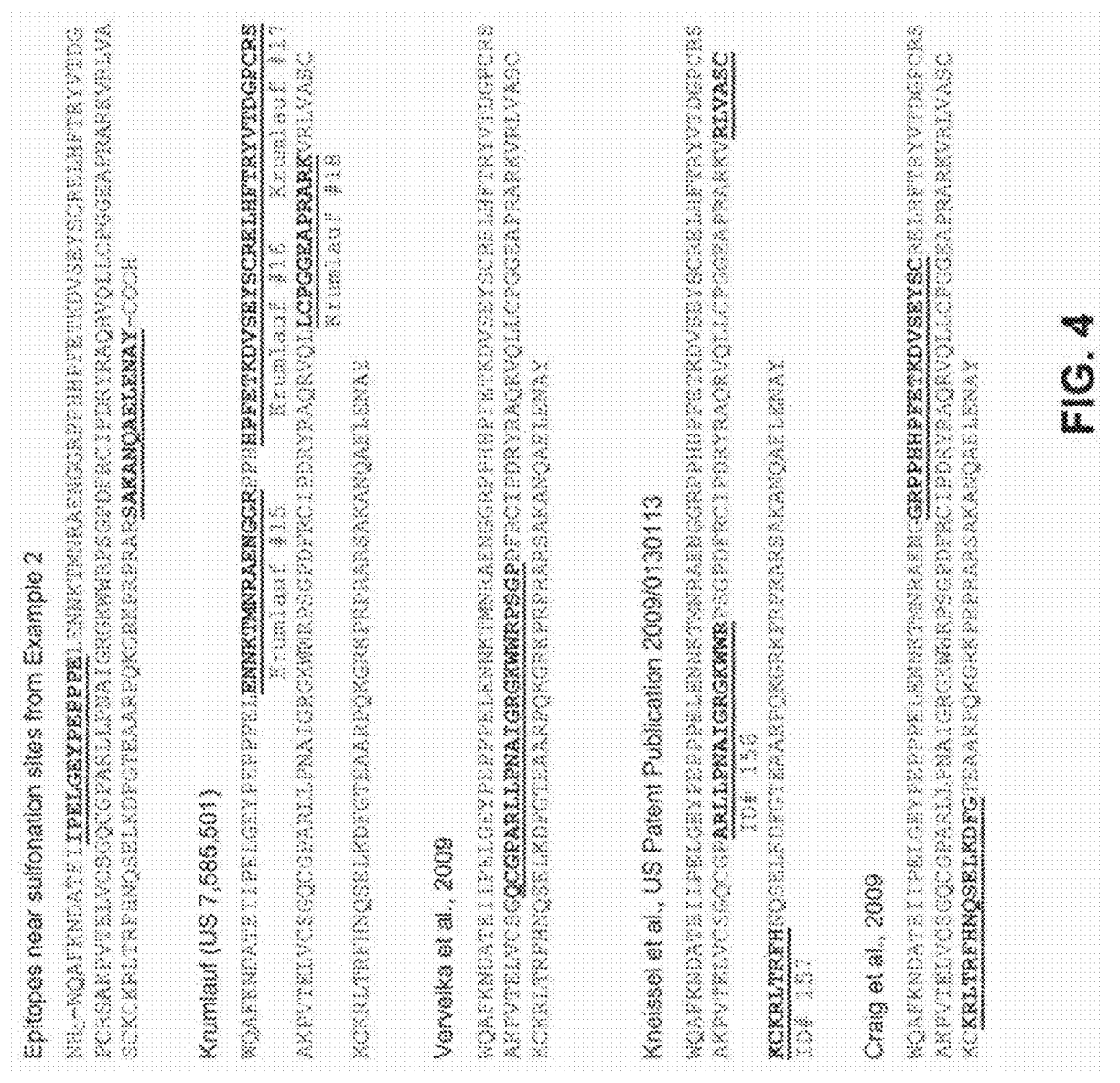

In one embodiment of the present invention, the epitope is five amino acids or greater. In another embodiment, the epitope encompasses ten or more amino acids. A comparison of the identity and location of potential epitopes of the present invention and sequences used as Sclerostin epitopes in prior art is given in FIG. 4. The underlined regions adjacent to Tyr$_{43}$ and Tyr$_{213}$ in FIG. 4 are only intended to render a visual aid in comparing the regions of the present invention with previously described art and not intended to delineate the epitope itself, or limit the epitopes to which the antibody binding site binds. Antibody binding sites may be generated that are specific for either the sulfated or unsulfated form of the protein and include the sulfation site (e.g., Tyr$_{43}$ or Tyr$_{213}$ of human Sclerostin, Tyr$_8$ of human Dvl1, Tyr$_{83}$ of human Dkk1, Tyr$_{175}$ or the Tyr$_{178}$ of human Kr1, Tyr$_{580}$ of human Fz6, or Tyr$_{380}$ or Tyr$_{1583}$ of human LRP5 and non-human equivalents thereof.

Although peptides may be used for the generation of linear epitopes, antibodies can also be found that recognize a three-dimensional set of determinants (sometimes referred to as interrupted epitopes or non-linear epitopes) and development and isolation of these types of antibodies can be carried out by using three-dimensional antigens such as the entire protein of interest or selected fragments as immunogens. Such antibodies may also be realized from screening of pre-formed libraries that are independent of an immunogen. Screening can then be carried out for an ability to distinguish between sulfated and unsulfated versions of the protein of interest. For a discussion on the use of conformationally derived epitopes, see Van Regenmortel 1998, J Immunol Methods 216:37-48; Villen et al., 2001 Biologicals 29:265-269; Moreau et al., 2006 Bioinformatics 22:1088-1095; and Huang and Honda 2006 BMC Immunology 7:7.

The protein comprising an antibody binding site of these embodiments may be prepared by any method known in the art including immunization followed by bleeding or spleen cell fusion with myeloma cell lines, and recombinant DNA technology including but not limited to phage display technology. See also Bundgaard et al., 2008 Methods Mol Bio 446:47-66; Hoffhiner et al., 2006; Kehoe et al. 2006; Craig et al., 2009 Hybridoma 28:377-381; U.S. Pat. No. 7,585, 501, US Patent Publication 2004/0009535 and US Patent Publication 2009/02130113, all of which are incorporated by reference. One source of antigens that may be used for this purpose is artificial peptides that represent the sulfated sequences, for example the peptides described above. The peptide or peptides used for immunization may be modified or unmodified, depending upon whether the antibody is desired to recognize the modified or unmodified epitope. Post-synthetic modifications can be carried out either chemically or by in vitro modification by a sulfotransferase, for example by the methods provided in the Examples below. Screenings of antibody libraries can then be carried out to determine the nature of the recognition such that it is specific for the sulfated version of the target protein, the unsulfated form or is independent of the state of sulfation. In addition to such custom libraries, pre-existing libraries such as the HuCal phage library is commercially available from AbD Serotec (Raleigh, N.C.) and is advertised as having more than 15 billion functional human antibody specificities. Another commercially available library comprises camelid derived antibodies and is available from Ablynx, Ghent, Belgium. These libraries have the advantage of not requiring any particular immunogen prior to screening. Screenings of this library may also be carried out as discussed above.

The presence of a sulfation group should in itself be sufficient to define part of an epitope. In an analogous fashion for another post-synthetic modification, the literature is replete with a large number of antibodies that are dependent on targets being either in phosphorylated or unphosphorylated forms and these form the basis of numerous assays for kinase activity. Furthermore, as described previously, the presence or absence of such small chemical moieties as a phosphate or sulfate group can have profound effects upon activity, thus validating the ability of biological partners to be able to recognize the differences between modified and unmodified forms. Specific examples of the search and identification of antibodies that are specific to epitopes of target proteins comprising a sulfated tyrosine have been described by Bundgaard et al., 2008, cited above. In a further example, an antibody (Mab15) that was selected for recognizing thyrotrophin receptor (TSHr) was found to have an epitope that was only found in mature forms of its target protein suggesting that some form of processing was required to create the appropriate epitope (Costagliola et al., 2002 EMBO J 21:504-513). In vivo treatment of cells with chlorate (which as mentioned earlier reduces sulfation modifications) resulted in production of a mature protein that was now unrecognizable by Mab15 indicating that the antibody was able to distinguish between the sulfated and unsulfated forms of its epitope and would only bind to the sulfated version. Thus, even though it was not originally selected for this feature, the use of sulfated antigens allowed isolation and identification of an antibody specific for a sulfate epitope in this target.

As discussed above, antibodies of this nature may also be used to evaluate in vitro assays of sulfation where they may be used to monitor conversion of the unsulfated form into the modified form. These antibodies may also be used alone or in conjunction with antibodies that recognize an epitope specific for the unsulfated form and/or for antibodies to an epitope in an amino acid sequence different from the sulfation sequence. Thus, for instance, an antibody that is specific for the sulfated form of the protein may be used in conjunction with an antibody that is specific for an unsulfated region of the protein for normalization purposes. In another example of use, an antibody that is specific for the unsulfated form can be used in conjunction with an antibody that recognizes the same region but essentially offers no discrimination between the sulfated and unsulfated forms of the antigen. Alternatively, two antibodies can be used where one is specific for the sulfated form and another is for the unsulfated form.

The proteins comprising an antibody binding site described above are useful for analytical or diagnostic purposes for evaluating the presence of sulfated proteins and/or the extent of sulfation. As described above, shifts in sulfation levels has previously been noted to be a feature of gastrin and cholcystokinin in cancer cells (Rehnfeld, 1990). The protein samples may be products that are excreted in the media or they may be derived from cell extracts. By these means, evaluation of physiological levels of sulfation of a Wnt pathway protein can be carried out with biological specimens. These may be used in a variety of ways to compare specimens that differ from each other in terms of origin, treatment or physiological conditions. An antibody specific for a sulfated form of a target protein may be used alone for this purpose or it may be combined in an assay that further includes an antibody directed towards the unsulfated form or an antibody that recognizes both sulfated and unsulfated forms. In reference to the latter, an ability to recognize both sulfated and unsulfated forms may be a property of an antibody that recognizes the epitope where the sulfation is located but is generically independent of the sulfation state, or it can an antibody that lacks relevance to the sulfation state by recognizing an epitope that is located outside of the modification region of the protein.

Thus, the present invention is also directed to a method of detecting or quantifying a sulfated Wnt pathway protein in a preparation. The method comprises combining the preparation with the protein comprising an antibody binding site described above under conditions allowing binding of the protein comprising an antibody binding site to the sulfated Wnt pathway protein in the preparation, then determining whether the protein comprising an antibody binding site is specifically bound to the sulfated Wnt pathway protein in the preparation. Any of the protein comprising an antibody binding site as described above can be used in this method, including but not limited to antibodies or antibody fragments.

These methods encompass the use of any immunological detection method described in the art, including immunoassays useful to detect the Wnt pathway protein in an extract of a biological tissue, including but not limited to ELISA, radioimmunoassay, and western blotting. Also encompassed within these methods are immunohistochemical methods for use in an intact tissue such as a fixed or unfixed tissue section. In some embodiments of these methods, the protein comprising an antibody binding site further comprises a detectable label, e.g., an enzyme, a fluorescent moiety or an electron dense moiety, as they are known in the art.

The antibody binding site can be directed against any Wnt pathway protein, for example a protein having a native sulfation site or a protein that is engineered to have such a site. Nonlimiting examples of proteins from which the peptide can be derived are a Sclerostin, a Dvl1, a Dkk1, a Kr1, a Fz6, an LRP5, a Wnt, a Dvl2, a Dvl3, a Dkk2, a DKK3, a DKK4, a Kr2, a Fz1, a Fz2, a Fz3, a Fz4, a Fz5, a Fz7, a Fz8, a Fz9, a Fz10, an LRP4, an LRP6 or any other Wnt pathway protein now known or later discovered.

The present invention also provides therapeutic methods using the compositions described above for treatment of a variety of diseases exacerbated by Wnt activation or inhibition. Nonlimiting examples of diseases exacerbated by Wnt activation include rheumatoid arthritis, a cancer, anemia, immune deficiency, high bone mass, hyperparathyroid tumor, caudal duplication syndrome, tooth agenesis, familial adenomatous polyposis, diabetic retinopathy, retinal inflammation, vascular leakage, and Wilms tumor. Nonlimiting examples of diseases exacerbated by Wnt inhibition include osteoporosis, osteopenia, osteomalacia, osteogenesis imperfecta, avascular necrosis (osteonecrosis), poor healing of implants, bone loss due to other disorders, periodontal disease, osteoarthritis, arthritis, and the formation and/or presence of osteolytic lesions, a cancer, type II diabetes, hair loss, inadequate production of stem cells, acute or chronic glomerulonephritis, rapidly progressive glomerulonephritis, nephrotic syndrome, focal proliferative glomerulonephritis, systemic lupus erythematosus, Goodpasture's syndrome, polycystic kidney disease, acute tubular necrosis, acute renal failure, polycystic renal disease, medullary sponge kidney, medullary cystic disease, nephrogenic diabetes, renal tubular acidosis, a tubulointerstitial disease, acute and rapidly progressive renal failure, chronic renal failure, nephrolithiasis, gout, hypertension, nephrosclerosis, microangiopathic hemolytic anemia, atheroembolic renal disease, diffuse cortical necrosis, renal infarcts, angina pectoris, myocardial infarction, chronic ischemic heart disease, hypertensive heart disease, pulmonary heart disease, rheumatic fever, rheumatic heart disease, endocarditis, mitral valve prolapse, aortic valve stenosis, valvular and vascular obstructive lesions, atrial or ventricular septal defect, patent ductus arteriosus, myocarditis, congestive cardiomyopathy, hypertrophic cardiomyopathy, X-linked focal dermal hypoplasia, tetra-amelia, Mullerian-duct regression and viriliation, Fuhrmann syndrome, odonto-onchyo-dermal hypoplasia, obesity, XX sex reversal with palmoplanter hyperkeratosis, autosomal recessive anonychia, hyponychia congenita, Van Buchem disease, or familial exudative vitreoretinopathy. See, e.g., MacDonald et al., 2009, Dev. Cell 17:9-26; Polakis, 2000, Genes Dev. 14:1837-1851; Chen et al., 2009, Am. J. Pathol. 175:2676-2685.

With respect to particular Wnt pathway proteins targeted in these therapeutic embodiments, Sclerostin and Dkk1 (both antagonists of Wnt signaling) are particularly useful targets since those two proteins are soluble proteins that interact with LRP5/6 in the intercellular space. Thus, administering either of these soluble proteins to a subject would be expected to increase their Wnt-inhibiting effect (i.e., decrease Wnt signaling). Further, since sulfation increases the Wnt-inhibiting effect of these proteins, administration of the sulfated forms would be expected to be more effective than administration of unsulfated or mixed sulfated and unsulfated forms. Conversely, administration of antibodies to either protein to a subject would be expected to decrease their Wnt-inhibiting effect (i.e., increase Wnt signaling). Administration of antibodies directed against Kr1 (also an antagonist of Wnt signaling) should also provide therapeutic value.

Furthermore, with respect to Sclerostin, although the binding of Sclerostin to an LRP receptor is responsible for biological effects, it is also known that Sclerostin interacts with other proteins such as BMPs (Bone Morphogenic Proteins) (Winkler et al., 2003 EMBO J 22:6267-6276), Noggin (Winkler et al., 2004 J Biol Chem 279:36293-36298) and "Cysteine-rich protein 61" (Craig et al 2010 (BBRC 392:36-40). As such, the discovery of the sulfated amino acids in Sclerostin allows application of the present invention to interactions between Sclerostin and these other proteins as well as the interactions with LRP receptors.

Thus, in some embodiments, the instant invention is directed to a method of treating a subject having a disease exacerbated by Wnt activation. The method comprises obtaining a Wnt pathway protein that inhibits Wnt activation and comprises a sulfation site; treating the Wnt pathway protein with a sulfotransferase that causes sulfation of the Wnt pathway protein; and administering the treated Wnt pathway protein to the subject. By treating the Wnt pathway protein with a sulfotransferase prior to administration, complete sulfation of the protein is assured to provide maximum Wnt inhibiting activity.

In preferred embodiments, the sulfated Wnt pathway protein is administered in a pharmaceutically acceptable excipient. By "pharmaceutically acceptable" it is meant a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, and the like.

The above-described proteins can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfate and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the subject a therapeutically effective amount of the compound. As used herein, nasally administering or nasal administration includes administering the compound to the mucous membranes of the nasal passage or nasal cavity of the patient. As used herein, pharmaceutical compositions for nasal administration of the composition include therapeutically effective amounts of the protein prepared by well-known methods to be administered, for example, as a nasal spray, nasal drop, suspension, gel, ointment, cream or powder. Administration of the protein may also take place using a nasal tampon or nasal sponge.

Where the composition is administered peripherally such that it must cross the blood-brain barrier, the composition is preferably formulated in a pharmaceutical composition that enhances the ability of the compound to cross the blood-brain barrier of the mammal. Such formulations are known in the art and include lipophilic compounds to promote absorption. Uptake of non-lipophilic compounds can be enhanced by combination with a lipophilic substance. Lipophilic substances that can enhance delivery of the compound across the nasal mucus include but are not limited to fatty acids (e.g., palmitic acid), gangliosides (e.g., GM-1), phospholipids (e.g., phosphatidylserine), and emulsifiers (e.g., polysorbate 80), bile salts such as sodium deoxycholate, and detergent-like substances including, for example, polysorbate 80 such as Tween™, octoxynol such as Triton™ X-100, and sodium tauro-24,25-dihydrofusidate (STDHF). See Lee et al., Biopharm., April 1988: 3037.

In particular embodiments of the invention, the protein is combined with micelles comprised of lipophilic substances. Such micelles can modify the permeability of the nasal membrane to enhance absorption of the protein. Suitable lipophilic micelles include without limitation gangliosides (e.g., GM-1 ganglioside), and phospholipids (e.g., phosphatidylserine). Bile salts and their derivatives and detergent-like substances can also be included in the micelle formulation. The protein can be combined with one or several types of micelles, and can further be contained within the micelles or associated with their surface.

Alternatively, the protein can be combined with liposomes (lipid vesicles) to enhance absorption. The protein can be contained or dissolved within the liposome and/or associated with its surface. Suitable liposomes include phospholipids (e.g., phosphatidylserine) and/or gangliosides (e.g., GM-1). For methods to make phospholipid vesicles, see for example, U.S. Pat. No. 4,921,706 to Roberts et al., and U.S. Pat. No. 4,895,452 to Yiournas et al. Bile salts and their derivatives and detergent-like substances can also be included in the liposome formulation.

In various embodiments, the Wnt pathway protein is administered parenterally, e.g., intravenously.

The Wnt pathway protein can be treated with the sulfotransferase by any method known in the art. In some embodiments, the Wnt pathway protein is treated with the sulfotransferase in vitro. In other embodiments, the Wnt pathway protein is produced in a cell that further comprises the sulfotransferase. The cell in these embodiments can be a eukaryotic cell and/or a cell that expresses a recombinant sulfotransferase. The sulfotransferase in these embodiments is preferably a TPST1 or TPST2. The Wnt pathway protein can also be sulfated by chemical methods.

The Wnt pathway protein in these embodiments can be any inhibitory Wnt pathway protein that comprises a sulfation site, whether the sulfation site is native or not native to the protein. In preferred embodiments, the Wnt pathway protein is a Sclerostin or a Dkk1.

These methods are useful for the treatment of any disease, now known or later discovered, that is exacerbated by Wnt activation, including but not limited to rheumatoid arthritis, a cancer, anemia, immune deficiency, high bone mass, hyperparathyroid tumor, caudal duplication syndrome, tooth agenesis, familial adenomatous polyposis, diabetic retinopathy, retinal inflammation, vascular leakage, or Wilms tumor.

In other embodiments, the invention is directed to another method of treating a subject having a disease exacerbated by Wnt activation. This method comprises (a) obtaining the composition comprising a peptide consisting of a fragment of a Wnt pathway protein that is not the entire Wnt pathway protein, where the fragment is sulfated, as described above, and (b) administering the composition to the subject. As discussed above, the peptide can comprise amino acid analogs and can further comprise some amino acid changes from the native Wnt pathway protein.

In these embodiments, the Wnt pathway protein inhibits Wnt activation. Administration of such a peptide would be expected to effectively inhibit Wnt signaling. Preferably, the composition is formulated in a pharmaceutically acceptable excipient, as described above.

In various embodiments, the peptide is less than 75 amino acids long, as described above.

The peptide can be administered by any means known in the art, as described in the above discussion of pharmaceutically acceptable excipients. In some embodiments, the peptide is administered parenterally, e.g., intravenously.

The peptide can be a fragment of any inhibitory Wnt pathway protein that comprises a sulfation site, whether the sulfation site is native or not native to the protein. In preferred embodiments, the Wnt pathway protein is a Sclerostin or a Dkk1.

The peptide can be sulfated by any means known in the art, e.g., by treatment with a sulfotransferase in vitro or by producing the peptide in a cell that further comprises the sulfotransferase. The cell in these embodiments can be a eukaryotic cell and/or a cell that expresses a recombinant sulfotransferase. The sulfotransferase in these embodiments is preferably a TPST1 or TPST2.

These methods are useful for the treatment of any disease, now known or later discovered, that is exacerbated by Wnt activation, including but not limited to rheumatoid arthritis, a cancer, anemia, immune deficiency, high bone mass, hyperparathyroid tumor, caudal duplication syndrome, tooth agenesis, familial adenomatous polyposis, diabetic retinopathy, retinal inflammation, vascular leakage, or Wilms tumor.

The proteins comprising an antibody binding site that binds to a sulfated Wnt pathway protein, as described above, may find use as therapeutic reagents that disrupt interaction between the Wnt pathway protein and its binding partner, for example the binding of Sclerostin or Dkk1 to LRP5/6. In the case of antibodies that are specific for either sulfated or unsulfated forms, a finer degree of control can be exerted over physiological processes, since each type of antibody will be directed towards a subpopulation of the target protein. As such, an ability to target only the sulfated form will leave the activity of the unsulfated from intact and vice versa for an antibody to the unsulfated from. This is a level of discrimination that would not be produced by antibodies described previously for Wnt pathway proteins. On the other hand, an antibody of the present invention that is generic in the sense of being independent of the sulfation state of the Wnt pathway protein, may also have therapeutic utility because the sites where modifications take place may have more significance than previously recognized, and thus, these regions are novel epitopes that are useful as targets for immunotherapy.

Thus, the present invention is also directed to a method of treating a subject having a disease exacerbated by Wnt inhibition. The method comprises treating the subject with the protein comprising an antibody binding site to a sulfated epitope of a Wnt pathway protein as described above. In these embodiments, the Wnt pathway protein enhances Wnt inhibition. In some embodiments, the protein is an antibody or an antibody fragment.

The inhibitory Wnt pathway protein to which the antibody binding site is directed can be any such protein now known or later discovered, where the sulfated epitope is either native or engineered into the protein. In preferred embodiments, the Wnt pathway protein is a Sclerostin, a Dkk1, or a Kr1.

The protein comprising an antibody binding site can be administered by any means known in the art, as described in the above discussion of pharmaceutically acceptable excipients. In some embodiments, the protein is administered parenterally, e.g., intravenously.

These methods are useful for the treatment of any disease, now known or later discovered, that is exacerbated by Wnt inhibition, including but not limited to osteoporosis, osteopenia, osteomalacia, osteogenesis imperfecta, avascular necrosis (osteonecrosis), poor healing of implants, bone loss due to other disorders, periodontal disease, osteoarthritis, arthritis, and the formation and/or presence of osteolytic lesions, a cancer, type II diabetes, hair loss, inadequate production of stem cells, acute or chronic glomerulonephritis, rapidly progressive glomerulonephritis, nephrotic syndrome, focal proliferative glomerulonephritis, systemic lupus erythematosus, Goodpasture's syndrome, polycystic kidney disease, acute tubular necrosis, acute renal failure, polycystic renal disease, medullary sponge kidney, medullary cystic disease, nephrogenic diabetes, renal tubular acidosis, a tubulointerstitial disease, acute and rapidly progressive renal failure, chronic renal failure, nephrolithiasis, gout, hypertension, nephrosclerosis, microangiopathic hemolytic anemia, atheroembolic renal disease, diffuse cortical necrosis, renal infarcts, angina pectoris, myocardial infarction, chronic ischemic heart disease, hypertensive heart disease, pulmonary heart disease, rheumatic fever, rheumatic heart disease, endocarditis, mitral valve prolapse, aortic valve stenosis, valvular and vascular obstructive lesions, atrial or ventricular septal defect, patent ductus arteriosus, myocarditis, congestive cardiomyopathy, hypertrophic cardiomyopathy, X-linked focal dermal hypoplasia, tetra-amelia, Mullerian-duct regression and viriliation, Fuhrmann syndrome, odonto-onchyo-dermal hypoplasia, obesity, XX sex reversal with palmoplanter hyperkeratosis, autosomal recessive anonychia, hyponychia congenita, Van Buchem disease, or familial exudative vitreoretinopathy.

According to a further embodiment of the invention, the proteins, peptides or antibodies administered as described above may be employed as adjunct or adjuvant to other therapy, e.g. a therapy using a bone resorption inhibitor, for example as in osteoporosis therapy, in particular a therapy employing calcium, a calcitonin or an analogue or derivative thereof, e.g. salmon, eel or human calcitonin, calcilytics, calcimimetics (e.g., cinacalcet), a steroid hormone, e.g. an estrogen, a partial estrogen agonist or estrogen-gestagen combination, a SERM (Selective Estrogen Receptor Modulator) e.g. raloxifene, lasofoxifene, bazedoxifene, arzoxifene, FC1271, Tibolone (Livial®), a SARM (Selective Androgen Receptor Modulator), a RANKL antibody (such as denosumab), a cathepsin K inhibitor, vitamin D or an analogue thereof or PTH, a PTH fragment or a PTH derivative e.g. PTH (1-84) (such as Preos™), PTH (1-34) (such as Forteo™), PTH (1-36), PTH (1-38), PTH (1-31)NH2 or PTS 893. According to another embodiment, the antibodies of the invention may be employed in combination with other current osteoporosis therapy approaches, including bisphosphonates (e.g., Fosamax™ (alendronate), Actonel™ (risedronate sodium), Boniva™ (ibandronic acid), Zometa™ (zoledronic acid), Aclasta™/Reclast™ (zoledronic acid), olpadronate, neridronate, skelid, bonefos), statins, anabolic steroids, lanthanum and strontium salts, and sodium fluoride. When pharmacological agents of antibodies of the present invention are administered together with another agent, the two can be administered in either order (i.e. sequentially) or simultaneously.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1. In Vitro Sulfation of Sclerostin

Human Sclerostin (25 µg R&D Systems, Minneapolis, Minn.)) was reconstituted in 100 µl of 100 mM MES pH=7.0. Sulfation was carried out by mixing 50 µl (12.5 µg) human Sclerostin and 22.5 µl (10.0 µg) of human TPST1 (R&D Systems) with 125 µL of assay mix [78.87 mM MES pH 7.0, 2.5 mM $MgCl_2$, 2.5 mM $MnCl_2$ 1.25 mM $CaCl_2$ and 200 µM PAPS (Sigma)]. Incubation was carried out for 1.5 hrs at 37° C. Buffer was then exchanged into 10 mM Tris pH 7.5 using protein desalting spin columns (Pierce Biochemicals, Rockford, Ill.).

Example 2. Detection of Sulfation Modifications by MS Analysis

Peptides from the Sclerostin from Example 1 as well as untreated Sclerostin were digested with either trypsin or GluC and loaded onto a C18 column followed by injection into a LTQ mass spectrometer. In the first analysis, the mass spectrometer was instructed to make MS/MS of all eluting peptides. The resulting data was analyzed and three peptides from Sclerostin containing tyrosines were identified: LGEYPEPPPELE, YVTDGPCR and ANQAELENAY. In the second analysis, targeted analysis was performed where the mass spectrometer was instructed to only do MS/MS on masses corresponding to the putative sulfated tyrosine containing peptides. For the GluC sample, the mass spectrometer was set to perform MS/MS at m/z 725.6, the mass of the doubly charged peptide LGEYPEPPPELE plus sulfation, at a normalized collision energy for CID at 2%, 4% or 10% and an MS3 of the highest fragment in each of the three MS/MS. In the tryptic sample, MS/MS was performed at m/z 602.0, the mass of the doubly charged peptide ANQAELENAY plus sulfation, and at m/z 524.5, the mass of the doubly charged peptide YVTDGPCR plus sulfation, at a normalized collusion energy for CID at 2%, 4% and 10% and an MS3 of the highest fragment in each of the three MS/MS. Both peptides at m/z 725.6 and 602.0, corresponding to sulfated peptide LGEYPEPPPELE and ANQAELENAY, respectively, showed a neutral loss of 80 Da (40 Da for a 2+ ion) at 10% CE which suggests that these peptides were sulfated, whereas at 2% and 4%, the loss was not very pronounced (FIG. 1). The neutral loss fragments were subsequently fragmented and produced the expected MS/MS for the expected peptides. The MS/MS at m/z 524.5 did not show such a loss (data not shown). Essentially the same results were seen for both the untreated sclersotin and the Sclerostin from Example 1 indicating the presence of sulfation modifications in Sclerostin prior to the in vitro reaction with TPST-1 in Example 1. Furthermore, although a phosphate addition at this site would also result in a shift of ~80 kd higher weight, further tests showed that the modifications at these sites exhibited the chemical lability typical of a sulfation modification.

Example 3. Biological Effects of In Vitro Sulfation of Sclerostin

A) Effects of Sulfation on Binding of Sclerostin to LRP5
1) Preparation of Alkaline Phosphatase-Labeled LRP5 (Alk-Phos-LRP5)

293T cells were seeded into 9 cm dishes. The next day, each dish was transfected with 12 µg of LRP5R1/2AP construct using Lipofactamine Plus (Invitrogen, Carlsbad, Calif.) according to the manufacturer's instructions. LRP5R1/2-AP is a nucleic acid construct that expresses LRP5 extracellular domains 1 and 2 fused to alkaline phosphatase. 48 hours after transfection, the supernatant of the culture was collected as LRP5R1/2AP conditioned medium and concentrated 20 times using a Centricon unit (Millipore, Billerica, Mass.) and stored at −80° C.
2) Binding of AlkPhos-LRP5 to Sclerostin Various amounts of unmodified Sclerostin or the in vitro treated Sclerostin from Example 1 were diluted into 80 µl of TBST buffer and added to individual wells of 96 well plates. After overnight incubation, unbound proteins were removed after which point the coated plates were blocked with 3% nonfat milk in PBS. The plates were than decanted and 0.5×LRP5R1/2AP conditioned medium was added to the plates. After 2.5 hours, the conditioned medium was removed and the 96 well plates were washed five times for three minutes with TBST. The alkaline phosphatase activity in each well was then determined using the Tropix luminescence assay kit (Invitrogen, Carlsbad, Calif.).
3) Results of the Binding Assay As seen in FIG. 2, the Sclerostin treated in vitro with TPST showed a marked increase in the amount of AlkPhos-LRP5 bound to the plates when compared to the untreated Sclerostin. These results are best interpreted as evidence that there is an increase in the binding affinity of the treated protein compared to the starting material. These comparative results were repeated with the mouse versions of Sclerostin (not shown) and showed essentially similar results although the basal levels of the proteins were different for each source.

B) Effects of Sulfation on the Ability of Sclerostin to Block Wnt Induced Expression of Alkaline Phosphatase
1) Induction of Alkaline Phosphatase Activity Growing cultures of 10T1/2 cells were washed with PBS and trypsinized for 5 minutes. Cells were resuspended at a concentration of $6 \times 10^5$ cells/ml and 10 µl were seeded into individual wells of a Costar 96 well plate (Corning, Inc.). Wnt 3a and either the untreated Sclerostin or the Sclerostin from Example 1 were added and the plates were incubated at 37° C. for 24 hours. 50 µl of universal lysis buffer (from the Luciferase Reporter Gene Assay, Roche Applied Science, Indianapolis, Ind.) was added to each well at ambient temperature for 5 minutes. Detection of alkaline phosphatase was measured by the addition of 50 µl of ready-to-use CPSD with Sapphire Enhancer (Applied Biosystems) followed by an incubation at ambient temperature for 25 minutes.
2) Results of the Assay As seen in FIG. 3, the Sclerostin sulfated in Example 1 gave similar results compared to the untreated Sclerostin except at the highest level of Sclerostin input where there was a significantly (P=0.006) more efficient blockage of Wnt induced alk phos activity. This result for the highest level of Sclerostin may be a result of the increase in the binding affinity of the treated protein compared to the starting material as seen in FIG. 2.

It should be noted that the Sclerostin used in these experiments was derived from recombinant clones in eukaryotic cell lines. Consequently, as seen in the MS results in Example 2, there is a significant population of Sclerostin proteins that already have pre-existing sulfation modifications. Thus, the positive effects seen in the experiments above is the result of conversion of any remaining unsulfated forms into the sulfated version by TSPT-1.

Example 4. Evaluation of Sclerostin Sequences with "Sulfinator" Program

The "Sulfinator" program is an online methodology of predicting the presence of sites in proteins that are substrates for tyrosine sulfation (Monigatti et al. 2002 Bioinformatics 18; 769-770). It can be accessed at the website http://www.expasy.org/tools/sulfinator/ with documentation available at http://www.expasy.org/tools/sulfinator/sulfinator-doc.html. When this program was applied to the human Sclerostin sequence (UniProtKB Accession No. Q9BQB4), the amino acid sequence ELGEYPEPPPELENNK in the N terminal region of Sclerostin was identified as corresponding to a tyrosine sulfation site with sulfation taking place with $Tyr_{43}$ in agreement with the MS results from Example 2. The corresponding sequences in the mouse and rat are G<u>L</u>GEYPEPPPE<u>NNQTM</u> and G<u>LR</u>EYPEPP<u>Q</u>ELENNQ respectively (UniProtKB Accession No Q99P68 and Q99P67) where differences in the amino sequence are underlined. Evaluation of the mouse and rat Sclerostin sequences by the Sulfinator program revealed that the rat protein should also be sulfated (and at the corresponding Tyr residue) while the mouse sequence did not show a positive result. It should be noted, however, that part of the criteria used by the Sulfinator program is contextual neighboring amino acid sequences and when the oligopeptide GLGEYPEPPPENNQTM from the mouse Sclerostin sequences was independently tested, it was indicated as being potential site for sulfation. The loose structure at the amino terminal end of Sclerostin (to be discussed below) is likely responsible for the oligopeptide Sulfinator results of mouse Sclerostin being in agreement with the binding assay results.

The region of Sclerostin involved in binding to LRP5/6 is not precisely known. It has been described as "Finger 2" (~aa's 115-147) by Weidauer et al., (2009 BBRC 380:160-165) and "Loop 2" (~aa's 86-112) by Veverka et al., (2009 JBC 284:10,890-10,900) where amino acid assignments are based on the mature protein. It can be seen that neither putative location corresponds to the $Tyr_{43}$ sulfation site. Nonetheless, a visualization of the predicted 3-dimensional structure shows that $Tyr_{43}$ is part of a loosely organized peptide strand that could located in proximity with the binding site in "loop 2" predicted by Ververka et al. As such, it is possible that the amino terminal portion of Sclerostin also participates in binding of Sclerostin to LRP5/6 and sulfation may have effects on this particular protein/protein interaction. Further support is from U.S. Pat. No. 7,585,501 where the $Tyr_{43}$ site is a short distance away from an additional Sclerostin sequence (#15) that was described as participating in binding with LRP5/6. This point is illustrated further in FIG. 4.

Example 5. Peptides Derived From Sulfation Sites

Peptides from the sulfation modification sites regions may be useful in modulating protein-protein interactions between a sulfated protein and a binding partner. Thus, for example, the sequences ELGEYPEPPPELENNK and KANQAELENAY from Sclerostin can be used to artificially synthesize peptides that can be used as therapeutic compounds. Both modified and unmodified versions of these peptides can be made and tested to see which ones are more effective and if they are equivalent in potency.

Example 6. Development of Antibodies Specific for Sulfated Proteins

Antibodies that are specific for Sclerostin can be developed using peptides derived from the recognition sequences described in Examples 2 and 5. In FIG. 4, the sites previously described for use as epitopes for Sclerostin antibodies is compared with the sulfation sites described in Example 2. Unmodified peptides can be designed and obtained from numerous commercial sources. Post-synthetic modifications can then be carried out either chemically or by in vitro modification by TPST-1. These antigens can then be used to obtain antibodies using methods taught in Bundgaard et al., 2008; Hoffhiner et al., 2006; Kehoe et al. 2006; U.S. Pat. No. 7,585,501: US Patent Publication 2004/0009535; and US Patent Publication 2009/02130113. Screenings can be carried out to determine the nature of the recognition such that it is specific for sulfation of only the target protein. A similar program can be carried out with analogous peptides that remain unmodified; these can be used to obtain antibodies that are specific for the unmodified version of the targets. Screenings can also be based upon an ability to bind to the specific region of the Sclerostin sulfation, but the affinity of the protein is for both sulfated and unsulfated versions of the antigen target.

The discovery of a sequence in Sclerostin that comprises a sulfate modified tyrosine provides information concerning previously unknown epitopes in Sclerostin that may be used to generate novel antibodies that target these sites. For this purpose, a peptide can be used that comprises the sequence ELGEYPEPPPELE where the tyrosine is modified to comprise a sulfate group in order to generate an antibody that targets the sulfated tyrosine site at the amino end of Sclerostin. This modification can be carried out either chemically or by treatment with TPST-1 and PAPS. Another peptide, comprising the sequence KANQAELENAY (where the tyrosine is also modified by sulfation) can be used to generate an antibody to the sulfated tyrosine site at the carboxyl end of Sclerostin. Generation and isolation of an antibody can then be carried out by the methods described by Bundgaard et al., 2008 in conjunction with the methods taught in U.S. Pat. No. 7,585,501, US Patent Publication 20040009535 and US Patent Publication 20090130113, all of which are incorporated by reference.

When using a peptide with a sulfated tyrosine as the immunogen, resultant antibodies can display a variety of different affinities. For example, in an article giving the protocol for generating antibodies against peptides containing a phosphorylated tyrosine, the point is made: "Such an immunization will generate an immune response with at least four components: (1) anti-carrier protein reactivity, (2) general antiphosphotyrosine reactivity, (3) phosphorylation-independent anti-peptide reactivity and (4) phosphorylation-dependent anti-peptide reactivity." (DiGiovanna et al., 2002 Current Protocols in Cell Biology 16.6.1-16.6.18). As such, that article points out that even when using a peptide with the appropriate modification, antibodies can be generated that may only require the appropriate amino acid sequence and ignore the presence or absence of a modified tyrosine. Consequently, many of the past efforts to isolate an antibody against a phosphorylated peptide have included a counter-selection step to eliminate antibodies that bind to the unphosphorylated version of the target peptide/protein.

In contrast, although it is a goal of the present invention to generate and isolate antibodies that are specific for a protein that has a sulfated tyrosine, utility is also found during such a search to identify and isolate antibodies that are specific for the sulfated tyrosine site but that are also independent of the sulfation state of the target protein. Thus in parallel, identification processes can be carried out that initially are identified in terms of an the ability to bind to the region encompassed by the sulfation modifications and then a secondary screening can be carried out for a) antibodies that have the ability to detect only epitopes that include the sulfation modification and b) antibodies that are independent of the sulfation status of the target region.

Example 7. Growth of Sclerostin in Cells Treated with Chlorate and Subsequent Testing in Binding Assay 1. Production of Human Sclerostin After amplification with the forward primer CAGGGGTGGCAGGCGTTCAA and the reverse primer GTAGGCGTTCTCCAGCTCGG, the human Sclerostin PCR product with blunt ends was cloned into pFastBac/HEM-TOPO vector (Invitrogen). The recombinant plasmid was transformed into the DH10Bac™ E. coli strain. A transposition subsequently took place between the mini-Tn7 element on the pFastBac/HBM recombinant plasmid and the mini-attTn7 target site on the baculovirus shuttle vector in the presence of transposition proteins from the helper plasmid, generating a recombinant bacmid. The recombinant bacmid DNA was prepared and transfected into the Sf9 insect cell line with the Cellfection II™ reagent (Invitrogen), from which the recombinant baculovirus expressing human Sclerostin was produced. Human Sclerostin was produced in High Five™ insect cells (Invitrogen) infected with the recombinant baculovirus.

Figure 5:
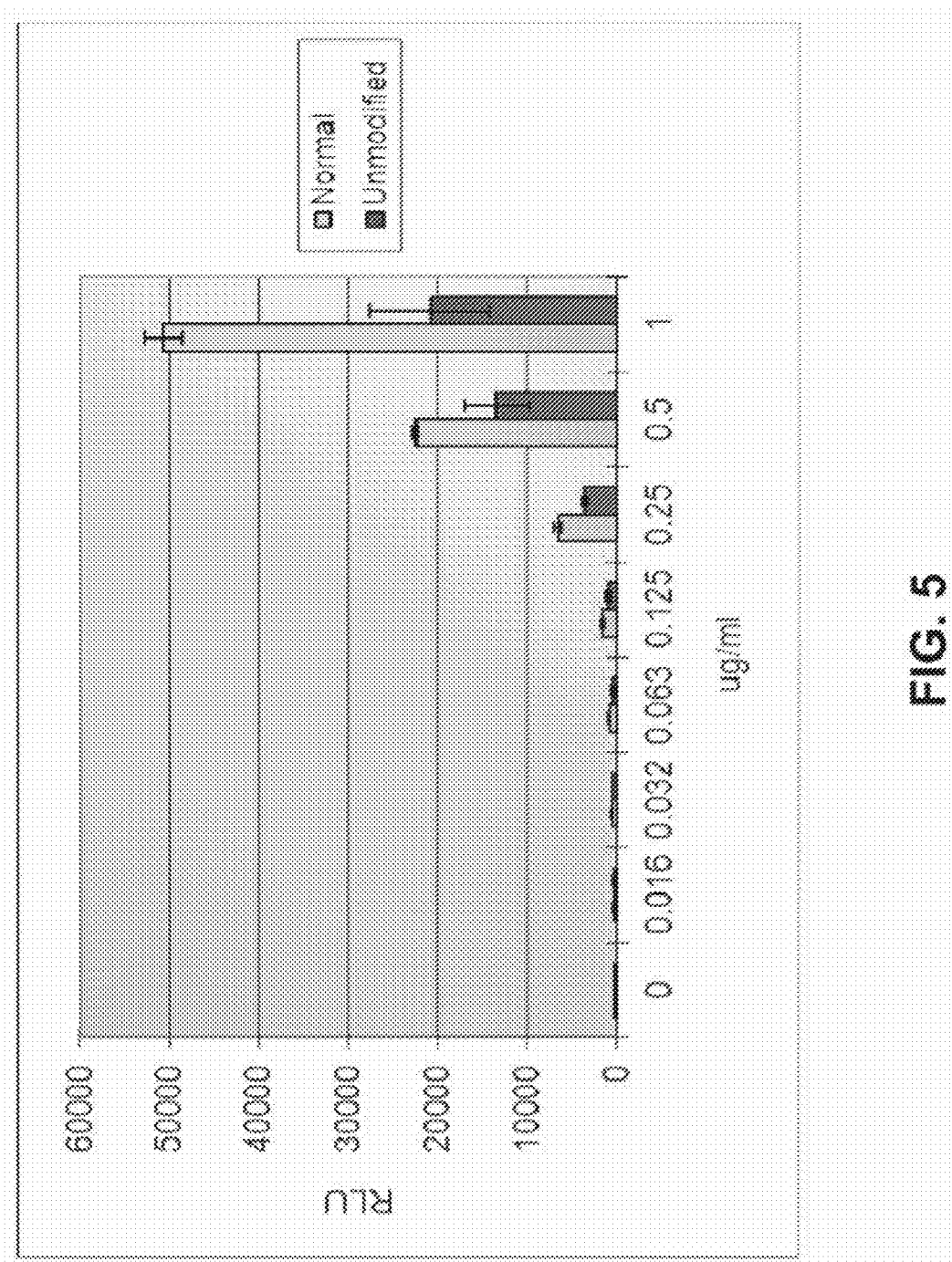
FIG. 5 shows the binding of an alkaline phosphatase-LRP5 fusion to sulfated Sclerostin ("Normal") vs. chlorate-treated Sclerostin ("Unmodified").

2. Preparation of Sclerostin in Insect Cells Treated with Chlorate and Subsequent Testing in Binding Assay
A. Preparation of Sclerostin in Insect Cells Treated with Chlorate The SF9 cells described above were harvested, counted and diluted by Sf-900 II SFM growth medium. The cells were distributed into 15 cm tissue culture dishes to reach 70-80% confluence and cultured for 6 hours. The baculovirus expressing Sclerostin was added into the cells at 0.2 MOI. Infected Sf9 cells were cultured in the dishes at 28° C. for 72 hrs. Culture medium was collected, centrifuged at 1200 rpm for 25 minutes, and the supernatant was transferred into 50 ml tubes and kept at 4° C. A plaque assay was performed to determine the titer of the Sclerostin-expressing baculovirus which was adjusted to ~$10^7$/ml with Express Five™ Serum Free Medium. High Five™ cells were harvested, counted and diluted into Express Five™ Serum Free Medium (Invitrogen). Sclerostin-expressing baculovirus was added to the High Five™ cells at 2 MOI, and the cell density was adjusted to $10^6$/ml in Express Five™ Serum Free Medium. After mixing, the cells were divided into two treatments. To one treatment, chlorate was added to a final concentration of 1 mM. The other treatment lacked chlorate. Each cell suspension was aliquoted into eight 250 ml flasks, 100 ml/flask. The flasks were placed in a shaker at 28° C. and 100 rpm for 48 hr. The cell suspension was then collected by centrifugation at 1500 rpm for 20 minutes and pooled. A total of 800 ml of supernatant was collected and frozen at −80° C. Elution Buffer A (25 mM imidazole in PBS+0.5% CHAPs) and B (400 mM imidazole in PBS+0.5% CHAPs) were prepared 50 ml Elution Buffer A was combined with 7.5 ml Ni-NTA agarose and the mixture was loaded onto a column. 800 ml of frozen conditioned medium was thawed. CHAPS (4 g) was added to the supernatant to reach a concentration of 0.5% CHAPS. The collected supernatant was loaded onto the Ni-NTA agarose column and eluted at ~2 ml/min. After the supernatant was completely loaded onto the column, the column was washed with 100 ml Buffer A at 2 ml/min to wash out the unbound proteins. After washing, Sclerostin was eluted from the column with 10 ml Buffer B. The Sclerostin solution was loaded on to a centrifugal filter unit, after which PBS+0.5% CHAPS was added to make the total volume 15 ml in the filter unit. The filter unit was then centrifuged at 3000 rpm for 10 min. The centrifugation step was repeated three times. The Sclerostin solution in the centrifugal filter unit was collected and dried by lyophilization.
B. Sclerostin Binding Assay Stock solutions of 0.1 µg "Normal" (sulfated) and "Unmodified" (chlorate treated) Sclerostin/ml in PBS was prepared. 50 µl of the stock solution was diluted into 4000 µl PBS and 40 µl was loaded into each well of a microtiter plate to coat the plate with Sclerostin. The assay was then carried out essentially as described in Example 3(A).
C. Results Results are shown in FIG. 5. As shown therein, the "Normal" sulfated Sclerostin bound more LRP5 than the "Unmodified" chlorate treated Sclerostin.

Example 8. Reversal of Properties of Sclerostin Derived From Chlorate Treated Cells by Carrying Out In Vitro Sulfonation with TPST-1

MES buffer (0.1 M MES, 0.5% Triton X100, 2.5 mM $MgCl_2$, 2.5 mM $MnCl_2$, 1.25 mM $CaCl_2$, 0.75 mg/mL BSA, pH 7.0) was prepared. PAPS (3'-phosphoadenosine-5'-phosphosulfate—the sulfate donor in the TPST sulfation reaction) and TPST1 were dissolved in MES buffer to a concentration of 10 µM and 1 µg/ml, respectively. Sclerostin derived from chlorate-treated cells as described in Example 7 (50 µl) was added to each well, along with 50 µl of either TPST1 and PAPS ("In vitro modified"), or "Unmodified" control of either TPST1 without PAPS or PAPS without TPST1. The plate was incubated at 37° C. for 1 hr. The Sclerostin binding assay was performed as described in Example 7.

Figure 6:
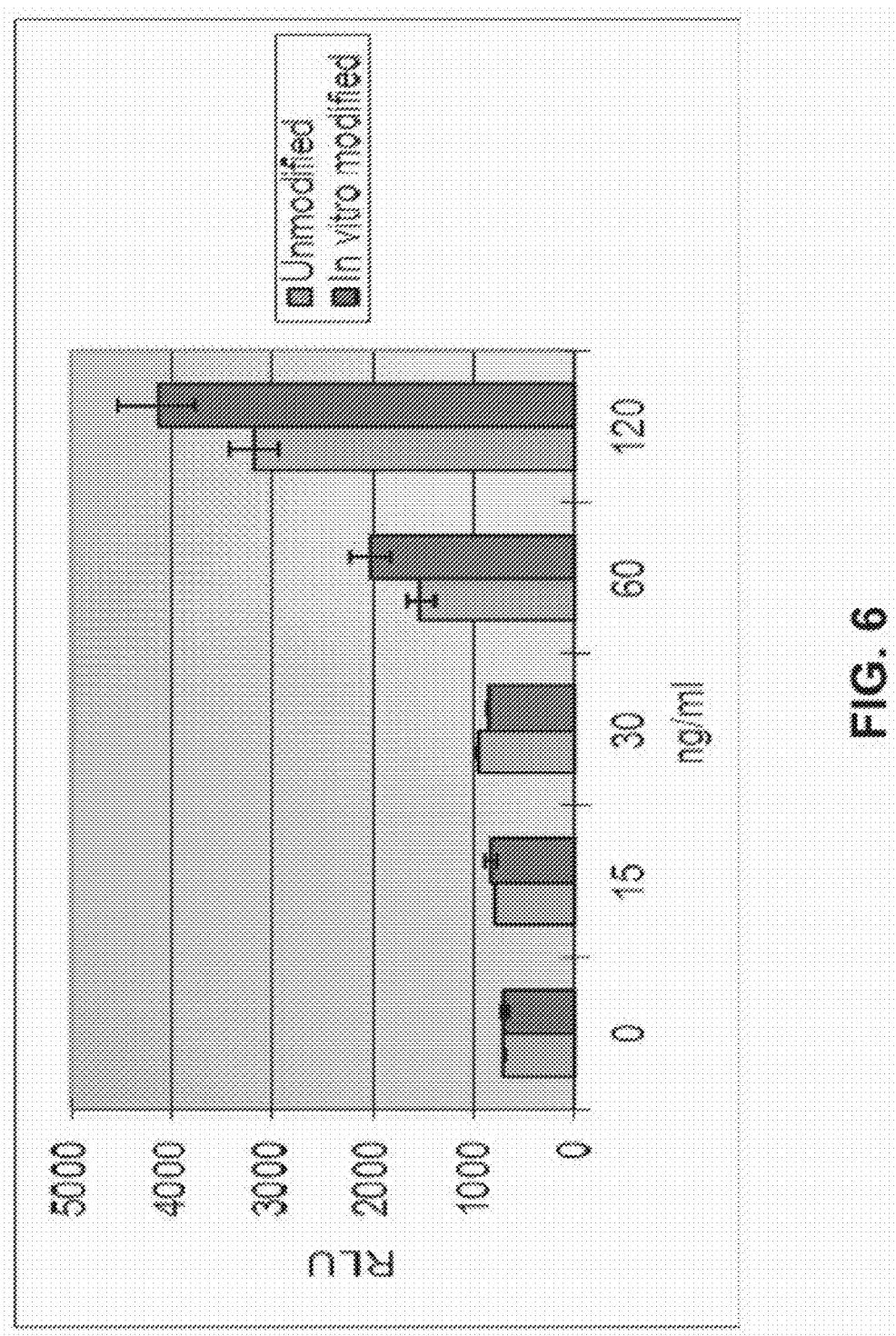
FIG. 6 shows the binding of an alkaline phosphatase-LRP5 fusion to chlorate-treated Sclerostin subsequently treated with PAPS only ("Unmodified") vs. chlorate-treated Sclerostin subsequently treated with TPST-1 and PAPS ("In vitro modified").
Figure 7:
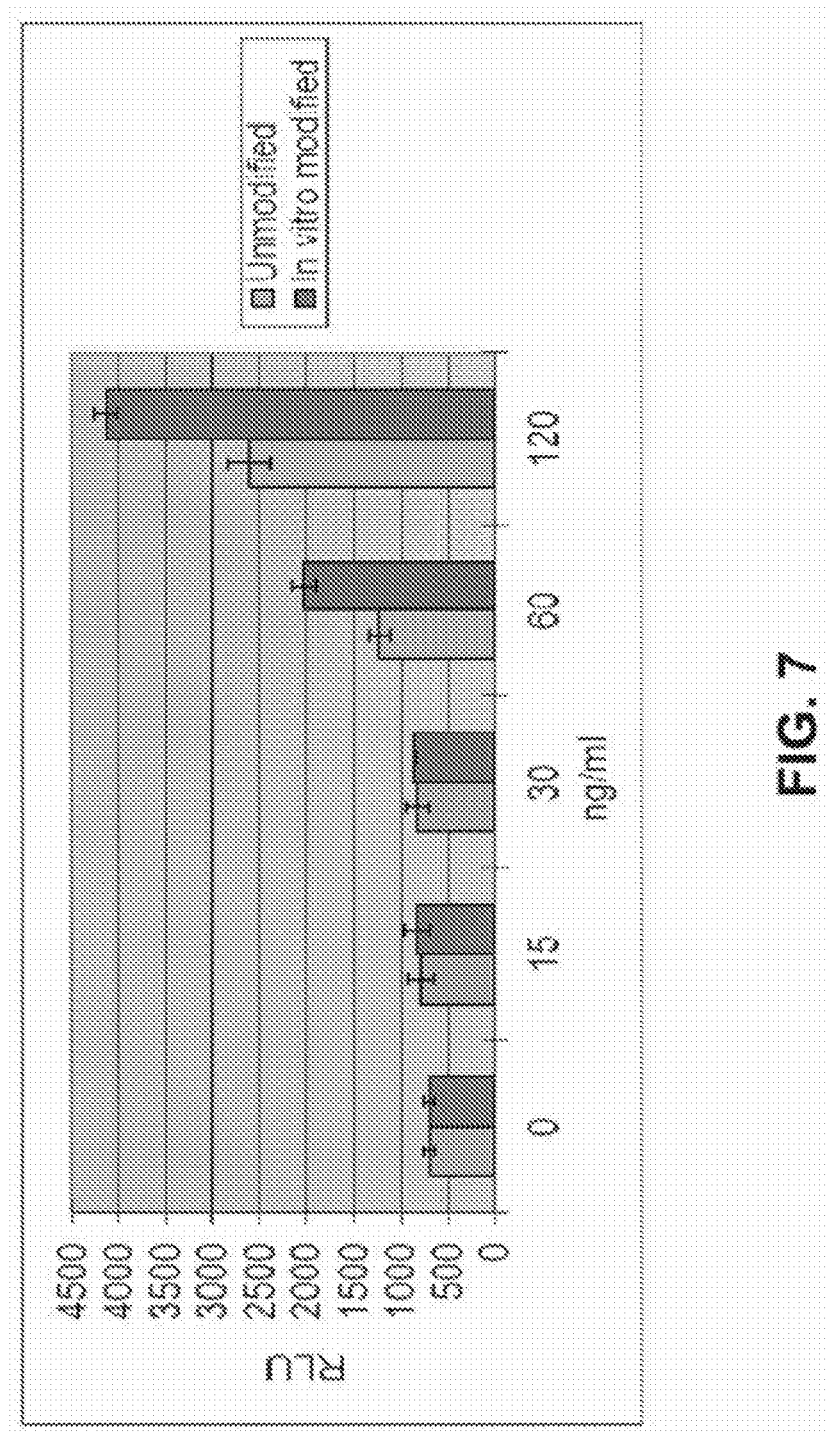
FIG. 7 shows the binding of an alkaline phosphatase-LRP5 fusion to chlorate-treated Sclerostin subsequently treated with TPST-1 only ("Unmodified") vs. chlorate-treated Sclerostin subsequently treated with TPST-1 and PAPS ("In vitro modified").

The results are shown in FIGS. 6 ("Unmodified" is PAPS only) and 7 ("Unmodified" is TPST1 only). As shown therein, treatment of the unsulfated Sclerostin with TPST1 and PAPS (causing sulfation of the Sclerostin) led to greater binding of the alkaline phosphatase-LRP5 fusion protein than the unsulfated Sclerostin treated with PAPS alone or TPST1 alone. This further confirms that sulfated Sclerostin has greater binding to LRP5 than unsulfated Sclerostin.

Example 9. Analysis of Several Wnt Pathway Proteins for Sulfation Sites Using Sulfonator The sulfonator program was used with a variety of different proteins involved in Wnt signaling including members of the Disheveled, Frizzled and Dkk families, as well as the LRP5 and LRP6 receptors. The sequences tested as well as the particular sites where sulfonation sites are predicted to be located are given below:
Dishevelled (Dvl)

| Human Dvl1 O14640 | IIYHMDEEE | Position 8 |
| Mouse Dvl1 P51141 | IIYHMDEEE | Position 8 |
| Human Dvl2 O14641 | No site predicted | |
| Mouse Dvl2 Q60838 | No site predicted | |
| Human Dvl3 Q92997 | No site predicted | |
| Mouse Dvl3 Q61062 | No site predicted | |

Conclusion: A potential tyrosine sulfation site was identified by Sulfinator in the DIX region of Dvl 1. The sequence is sufficiently conserved that it is identical in both human and mouse proteins. However, if Dishevelled is not processed through the Golgi apparatus, it will not be exposed to a TPST enzyme and will not be sulfated.
Dickkopf (Dkk)

| Human Dkk1 O94907 | DNYQPYPCAEDE | Position 83 |
| Mouse Dkk1 O54908 | DNYQPYPCAEDE | Position 84 |
| | DLDNYQPYP | Position 81 |
| (overlapping Tyr sites in mouse Dkk1) | | |
| Human Dkk2 Q9UBU2 | No site predicted | |
| Mouse Dkk2 Q9QYZ8 | No site predicted | |
| Human Dkk3 Q9UBP4 | No site predicted | |
| Mouse Dkk3 Q9QUN9 | No site predicted | |
| Human Dk4 Q9UBT3 | No tyrosines | |
| Mouse Dkk4 Q8VEJ3 | No site predicted | |

Conclusion: The $Tyr_{83}$ site in human Dkk1 is adjacent to but not part of the first Cysteine Rich Domain (CRD) of Dkk-1 and is found in both the human and mouse versions of Dkk1.
Kremen (Kr)

| Human Kr1 Q96MU8 | GNNFDYWKYGEA | Position 175 |
| | PDYWKYGEASS | Position 178 |
| Mouse Kr1 Q99N43 | No site predicted | |
| Human Kr2 Q8NCW0 | No site predicted | |
| Mouse Kr2 Q8K1S7 | No site predicted | |

Frizzled (Fz)

| | | | |
|---|---|---|---|
| Human Fz1 | Q9UP38 | No site predicted | |
| Mouse Fz1 | O70421 | No site predicted | |
| Human Fz2 | Q14332 | No site predicted | |
| Mouse Fz2 | Q9JIP6 | No site predicted | |
| Human Fz3 | Q9NPG1 | No site predicted | |
| Mouse Fz3 | Q61086 | No site predicted | |
| Human Fz4 | Q9ULV1 | No site predicted | |
| Mouse Fz4 | Q61088 | No site predicted | |
| Human Fz5 | Q13467 | No site predicted | |
| Mouse Fz5 | Q9EQD0 | No site predicted | |
| Human Fz6 | O60353 | ITSHDYLGQETLTEIQ | Position 580 |
| Mouse Fz6 | Q61089 | IADHDYLGQETSTEV | Position 580 |
| Human Fz7 | O75084 | No site predicted | |
| Mouse Fz7 | Q61090 | No site predicted | |
| Human Fz8 | Q9H461 | No site predicted | |
| Mouse Fz8 | Q61091 | No site predicted | |
| Human Fz9 | O00144 | No site predicted | |
| Mouse Fz9 | Q9R216 | No site predicted | |
| Human Fz10 | Q9ULW2 | No site predicted | |
| Mouse Fz10 | Q8BKG4 | No site predicted | |

Conclusion: No sites were identified by the Sulfonator program for human Fz1, Fz2, Fz3, Fz4, Fz5, Fz7, Fz8, Fz9 and Fz10 proteins. It should be noted that Position 580 of the Fz6 is in the cytoplasmic domain.

LRP Receptors

| | | | |
|---|---|---|---|
| Human LRP5 | O75197 | AIAIDYDPLEG | Position 380 |
| | | PHSQYLSAEDSCPPSP | Position 1583 |
| Mouse LRP5 | Q91VN0 | AIAIDYDPLEG | Position 379 |
| | | PHSQYLSAEDSCPPSP | Position 1582 |
| Human LRP6 | O75581 | No site predicted | |
| Mouse LRP6 | O88572 | TSDVNYDSEPVPPPTP | Position 1562 |
| Human LRP4 | O75096 | No site predicted | |
| Mouse LRP4 | Q8V156 | No site predicted | |

Conclusion: A single site is found in the extracellular portion of LRP5 and another site is found within the intracellular portion with sequences being identical for human and mouse in each case.

Neither LRP4 nor LRP6 are predicted to have sulfonation sites located on the extracellular portion; only the LRP5 receptor seems to have a site in the extracellular portion. Due to its extracellular location, the particular LRP5 site should be exposed and available for modification as part of the second YWTD domain (located at positions 341-602).

Example 10. Inhibition of Wnt by Sulfated Dkk1

Figure 8:
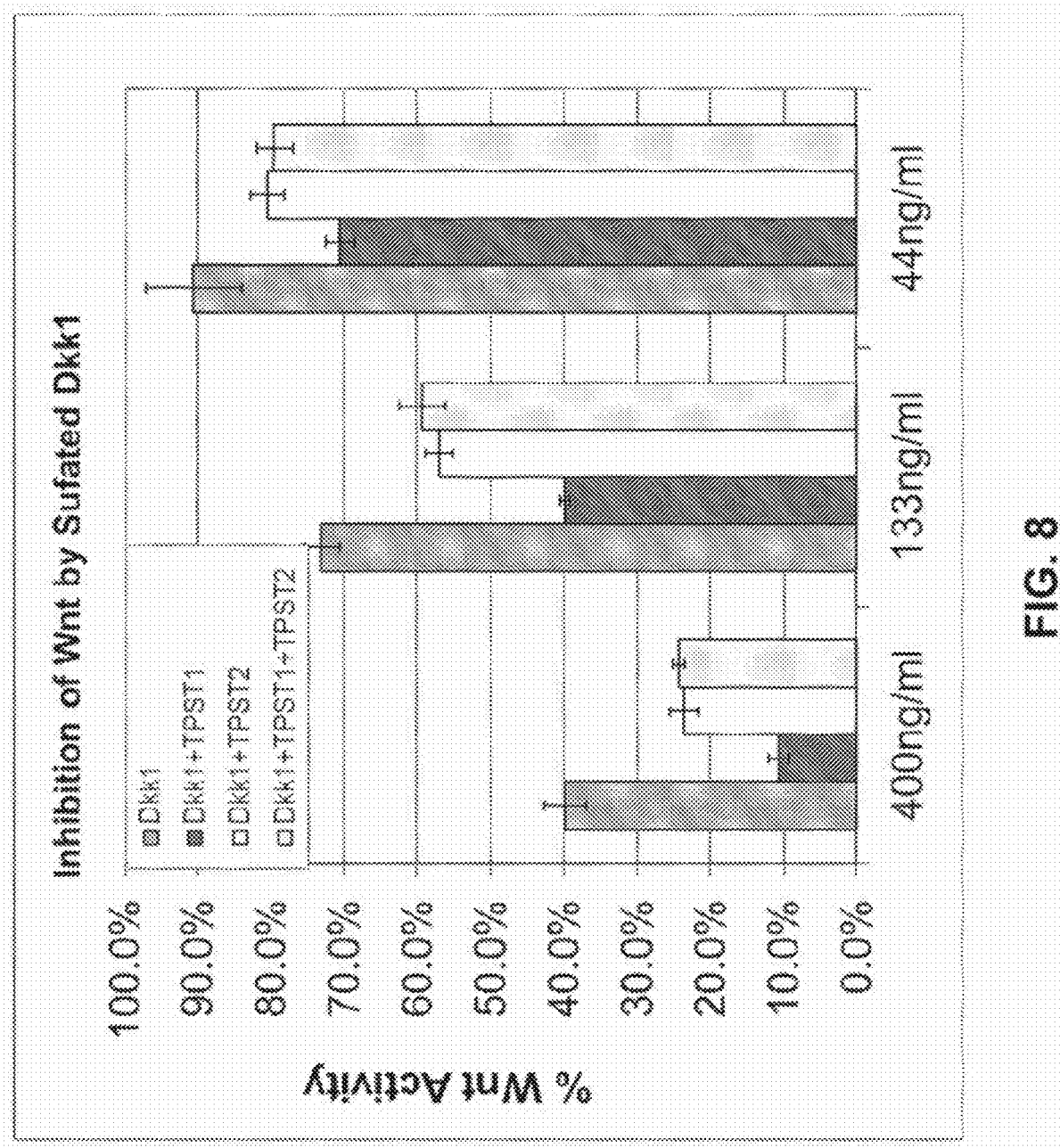
FIG. 8 shows the inhibition of Wnt activity after adding Dkk1, Dkk1+TPST-1, Dkk1+TPST-2, or Dkk1+TPST-1+TPST-2.

Native Dkk1 (having some sulfation) was untreated, or treated with either TPST1, TPST2 or both TPST1 and TPST2 to increase the sulfation of the Dkk1. These four Dkk1 preparations were used at three concentrations in the cell-based luciferase assay described in U.S. Patent Publication 2006/0198791 to determine the effect of sulfation on the ability of Dkk1 to inhibit Wnt signaling. The results are shown in FIG. 8. As shown therein, the three TPST-treated Dkk1 preparations inhibited Wnt activity to a greater degree than native Dkk1 alone. This establishes that sulfated Dkk1 inhibits Wnt signaling to a greater degree than unsulfated Dkk1.

FIG. 8 also shows that the TPST1-treated Dkk1 inhibited Wnt activity more than the other TPST-treated Dkk1 preparations, indicating that TPST1 is a more effective enzyme for sulfating Dkk1 than TPST2.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A composition consisting of isolated polyclonal antibodies or fragments thereof that specifically bind the peptide sequence ELGEYPEPPPELE (SEQ ID NO:9) when the tyrosine is sulfated and do not substantially bind said peptide sequence when the tyrosine is not sulfated, made by a process comprising the steps of:
   (i) immunizing a vertebrate with a synthetic peptide having the sequence ELGEYPEPPPELE (SEQ ID NO:9) wherein tyrosine is sulfated; and
   (ii) isolating polyclonal antibodies from the immunized vertebrate.

2. The composition of claim 1, comprising the fragments.

3. The composition of claim 2, wherein the fragments are Fab antibody fragments or an F(ab)$_2$ antibody fragments.

4. The composition of claim 1, wherein the vertebrate is a mouse, rabbit, sheep or goat.

* * * * *

UNITED STATES PATENT AND TRADEMARK OFFICE
CERTIFICATE OF CORRECTION

PATENT NO.        : 10,899,827 B2
APPLICATION NO.   : 15/273000
DATED             : January 26, 2021
INVENTOR(S)       : Joshua Rabbani and James J. Donegan Page 1 of 1

It is certified that error appears in the above-identified patent and that said Letters Patent is hereby corrected as shown below:

In the Claims

In Column 41, Line 51 (Line 2 of Claim 3), delete the word "an".

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*